(12) United States Patent
Ooi et al.

(10) Patent No.: US 12,193,740 B2
(45) Date of Patent: *Jan. 14, 2025

(54) METHOD AND SYSTEM FOR MEASURING OR ASSESSING HUMAN VISUAL FIELD

(71) Applicant: Ohio State Innovation Foundation, Columbus, OH (US)

(72) Inventors: Teng Leng Ooi, Columbus, OH (US); Chao Han, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,322

(22) Filed: May 30, 2023

(65) Prior Publication Data

US 2023/0301506 A1     Sep. 28, 2023

Related U.S. Application Data

(63) Continuation of application No. 16/888,038, filed on May 29, 2020, now Pat. No. 11,730,357, which is a continuation of application No. PCT/US2018/063283, filed on Nov. 30, 2018.

(Continued)

(51) Int. Cl.
*A61B 3/10*     (2006.01)
*A61B 3/02*     (2006.01)
(Continued)

(52) U.S. Cl.
CPC ............... *A61B 3/024* (2013.01); *A61B 3/08* (2013.01); *A61B 3/113* (2013.01); *G02B 27/017* (2013.01);
(Continued)

(58) Field of Classification Search
CPC .... A61B 3/10; A61B 3/00; A61B 3/14; A61B 3/02; A61B 13/00
(Continued)

(56) References Cited

U.S. PATENT DOCUMENTS 7,665,847 B2    2/2010   Alster et al.
10,463,246 B2   11/2019   Garoon et al.
(Continued)

FOREIGN PATENT DOCUMENTS

WO     2015/145111 A2     10/2015

OTHER PUBLICATIONS

International Search Report and Written Opinion issued by the International Searching Authority (ISA/US) in PCT Application No. PCT/US2018/063283 on Feb. 11, 2019. 8 pages.

*Primary Examiner* — Dawayne Pinkney
(74) *Attorney, Agent, or Firm* — Meunier Carlin & Curfman

(57) ABSTRACT

The exemplified systems and methods disclosed herein involve the contemporaneous and concurrent stimulation of both eyes of a patient with dissimilar visual scenes that substantially span an expected or normal visual field of both eyes. During an assessment via the exemplified system and methods, a test eye (i.e., eye being assessed) is presented a visual scene that is rich in contours (e.g., a scene with rich texture patterns) that substantially span an expected or normal visual field of a person while the non-tested eye is presented an impoverished visual scene (e.g., a contour-free or non-distinguishing-contour scene, e.g., with a homogeneous color, with respect to the contour-rich scene). Defects in the visual field can be detected by assessing for breaks or discontinuity in the observation of the contour-rich scene by the person.

19 Claims, 37 Drawing Sheets
(32 of 37 Drawing Sheet(s) Filed in Color)

Related U.S. Application Data

(60) Provisional application No. 62/592,568, filed on Nov. 30, 2017.

(51) Int. Cl.
*A61B 3/024* (2006.01)
*A61B 3/08* (2006.01)
*A61B 3/113* (2006.01)
*A61B 3/12* (2006.01)
*G02B 27/01* (2006.01)
*G06F 3/01* (2006.01)

(52) U.S. Cl.
CPC ...... *G06F 3/013* (2013.01); *G02B 2027/0134* (2013.01); *G02B 2027/0178* (2013.01)

(58) Field of Classification Search
USPC ............... 351/200, 203, 205, 206, 209–211, 351/221–223, 237–239, 246; 600/558
See application file for complete search history.

(56) References Cited

U.S. PATENT DOCUMENTS

| | | | |
|---|---|---|---|
| 11,291,362 B2 | 4/2022 | Arnold et al. | |
| 2010/0283969 A1* | 11/2010 | Cooperstock | A61B 3/022 |
| | | | 351/201 |
| 2013/0044290 A1* | 2/2013 | Kawamura | A61B 3/024 |
| | | | 351/239 |
| 2015/0282704 A1 | 10/2015 | Maddess et al. | |
| 2016/0089017 A1 | 3/2016 | Wang et al. | |
| 2016/0128893 A1 | 5/2016 | Ooi et al. | |
| 2016/0324416 A1 | 11/2016 | Fateh | |
| 2017/0127970 A1* | 5/2017 | Doran | A61B 3/14 |
| 2018/0214339 A1 | 8/2018 | Levi et al. | |
| 2019/0150727 A1 | 5/2019 | Blaha et al. | |
| 2021/0330185 A1* | 10/2021 | Krukowski | A61B 3/028 |

* cited by examiner

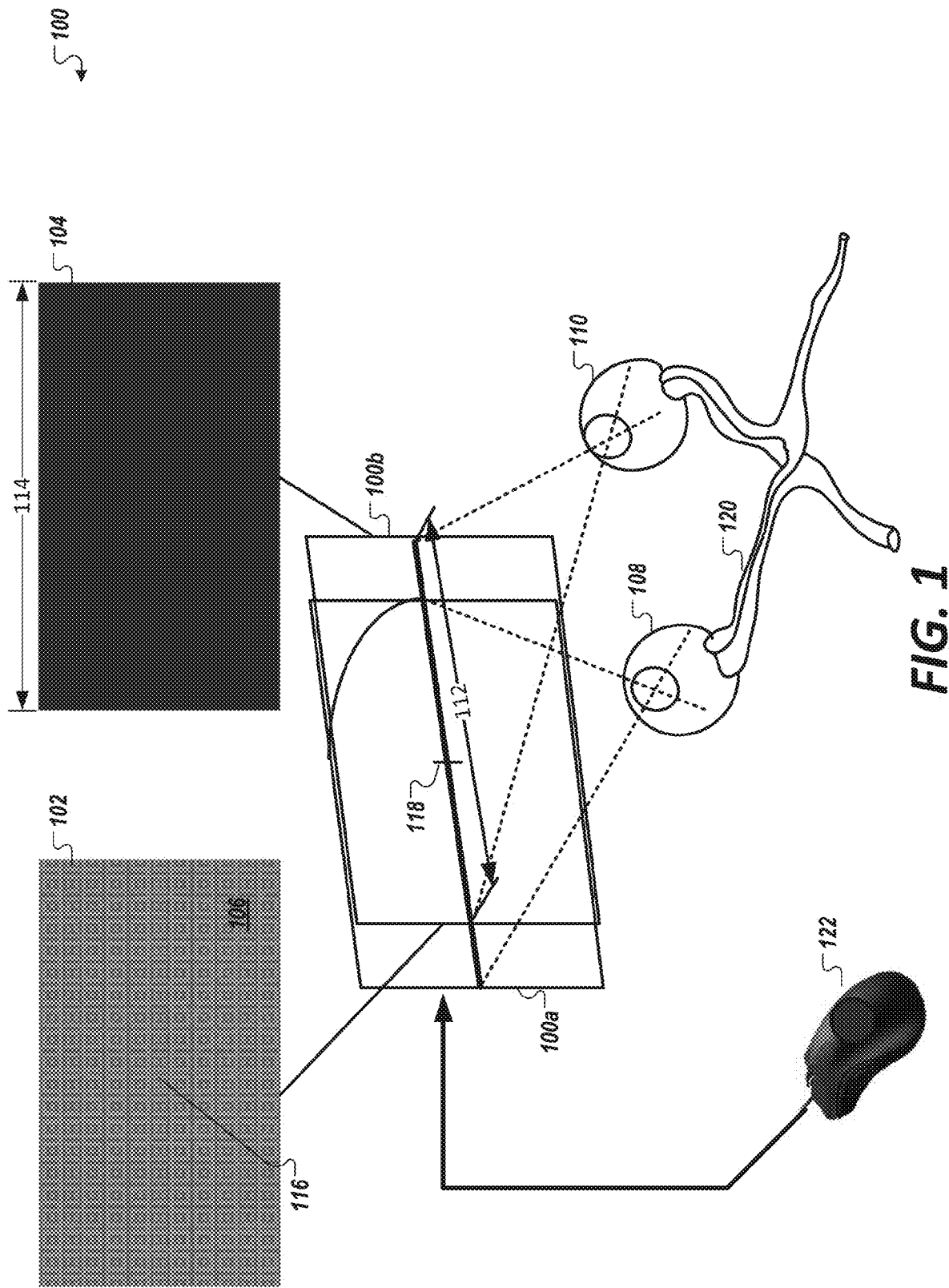

| Subject ID | Age | Visual Condition | logMAR VA both eyes | logMAR VA right eye | logMAR VA left eye |
|---|---|---|---|---|---|
| 2008 | 32 | retinitis pigmentosa | 0.16 | 0.12 | 0.18 |
| 2000 | 78 | glaucoma, diabetic retinopathy | 0.32 | 0.36 | 0.26 |
| 2009 | 45 | glaucoma suspect | -0.08 | -0.08 | -0.06 |
| 2016 | 54 | stargard's disease | 1.04 | 1.22 | 1.06 |

FIG. 12

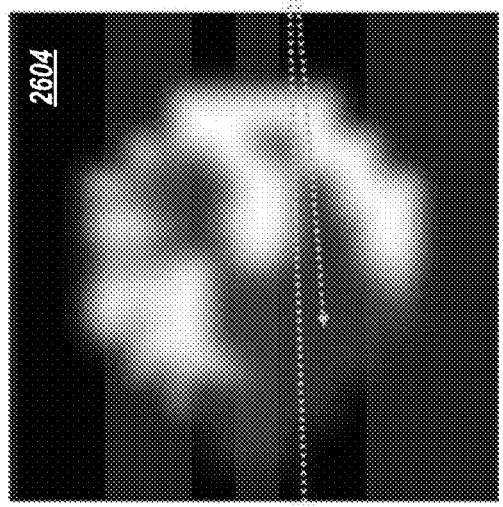
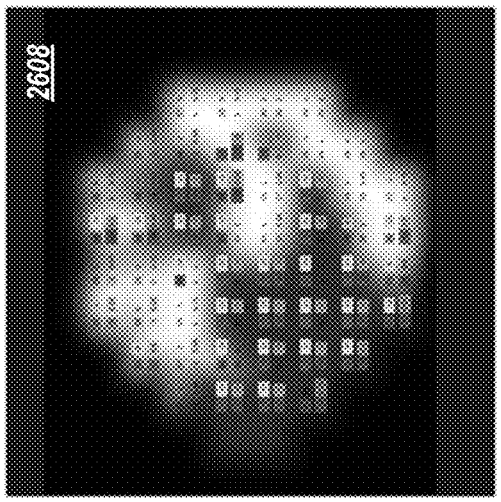
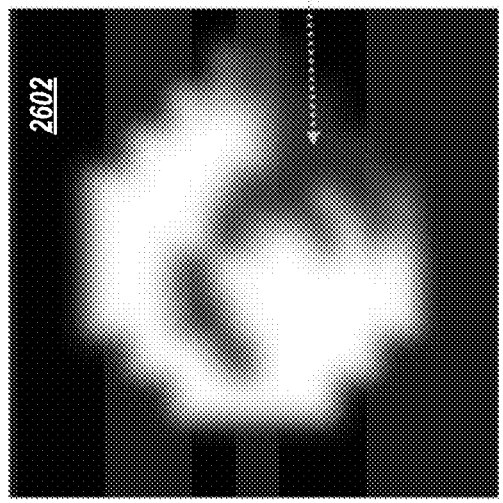
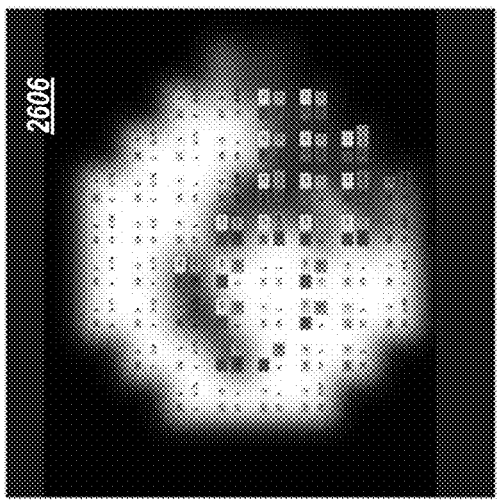
BVF mapping alone
darker areas indicate VF losses
BVF mapping superimposed on HVF mapping
note correspondence between BVF and HVF (i.e., dark areas overlap with colored quartets)
FIG. 26

Data from recollection response protocol

Data from eye tracking control protocol

Data from second proof-of-concept experiment

METHOD AND SYSTEM FOR MEASURING OR ASSESSING HUMAN VISUAL FIELD

CROSS-REFERENCE TO RELATED APPLICATIONS

This is a continuation application of U.S. Non-Provisional Application No. 16/888,038, filed May 29, 2020, entitled "METHOD AND SYSTEM FOR MEASURING OR ASSESSING HUMAN VISUAL FIELD", which is a continuation application of PCT patent application no. PCT/US2018/063283, filed Nov. 30, 2018, entitled "METHOD AND SYSTEM FOR MEASURING OR ASSESSING HUMAN VISUAL FIELD," which claims priority to, and the benefit of, U.S. Provisional Application No. 62/592,568, filed on Nov. 30, 2017, titled "METHOD AND SYSTEM FOR MEASURING OR ASSESSING HUMAN VISUAL FIELD," each of which is hereby incorporated by reference herein in its entirety.

BACKGROUND

Patients with diseases affecting the eye and brain are susceptible to losing parts of their visual field of view. For instance, disease like macular degeneration can cause central visual field loss while disease like glaucoma can cause peripheral visual field loss. Stroke patients can develop sector visual field loss. Eye doctors can often measure on a routine basis a patient's extent of visual-field loss to make diagnostic and therapeutic decisions. Once diagnosed with a disease, doctors can continue to measure visual field to monitor both the progression of the disease and the efficacy of prescribed medication or therapy. Conventional protocols and practice for measuring a person's field of view typically require complex instrumentation and are often performed by trained professional at a doctor's office.

Individuals may have compromised vision in one eye, or both, and may not be aware of such condition as the fellow eye if having an intact visual field at a same area as the compromised eye can mask or accommodate the condition. Nevertheless, compromised vision can degrade a person's quality of life in reducing the person's ability to perform daily activities and, in severe cases, in restricting his/her mobility. Although there are therapy options to address visual-field loss, compromised vision can go undiagnosed for long periods of time, e.g., which can be attributed in part to the frequency that screenings can be performed at a doctor's office.

SUMMARY

The exemplified systems and methods reduce complexities associated with the assessment of the visual field of a person. It can be used to augment, and in certain instances replace, existing practice and protocols to measure and/or assess visual-field loss as well. Further, it can also be used in self-measure protocols by a person to screen for visual-field loss and/or to monitor progression of visual-field loss of his/her own field of vision.

The exemplified systems and methods disclosed herein involve the contemporaneous and concurrent stimulation of both eyes of a patient with dissimilar visual scenes that substantially span an expected or normal visual field of both eyes. During an assessment via the exemplified system and methods, a test eye (i.e., eye being assessed) is presented a visual scene that is rich in contours (e.g., a scene with rich texture patterns) that substantially span an expected or normal visual field of a person while the non-tested eye is presented an impoverished visual scene (e.g., a contour-free or non-distinguishing-contour scene, e.g., with a homogeneous color, with respect to the contour-rich scene). Defects in the visual field can be detected by assessing for breaks or discontinuity in the observation of the contour-rich scene by the person. To this end, the exemplified systems and methods can detect visual field loss quickly by simultaneously assessing multiple and/or all regions of the visual field of an eye and without need of elaborate or complex instrumentation.

The visual images are viewed with a controlled vision device (also referred to as a 3D-vision device) that controls the separate presentation of the dissimilar visual scenes for each eye. In some embodiments, the dissimilar visual scenes are presented on an electronic display device (e.g., computer screen or tablet) or on printed material, and filtered eyewear (e.g., having color filters or polarizing filters) are used to separately present the dissimilar visual scenes to each of the eyes. In other embodiments, vision equipment (e.g., haploscopic devices, stereoscopic devices, or virtual-reality display devices) are used to separately present the dissimilar visual scenes to each eye.

In some embodiments, the visual scenes are presented dynamically with varying or modulating visual information and/or contrast. In some embodiments, the visual scenes are presented as a static presentation.

In an aspect, a method is disclosed, e.g., for measuring or assessing human visual field. The method includes stimulating both eyes of a person with dissimilar visual scenes (e.g., via a controlled vision device), wherein a first set of images (e.g., a single image or an animated sequence) is presented to a first eye (e.g., the left or right eye) of the person, wherein the first set of images comprises a pattern having one or more contour elements that span a substantial portion of a visual field of the first eye, and wherein a second set of images is contemporaneously presented to a second eye (e.g., the other eye) of the person, wherein the second set of images comprises a second pattern having either a different distinguishing contour elements to the first image or no distinguishing contour elements that spans a substantial portion of a visual field of the second eye (e.g., having a homogenous background); and, contemporaneous with the person fixating on a target on the first set of images (e.g., during presentation of the visual scenes or immediately after), directly or indirectly capturing one or more inputs (e.g., via an electronic display to which the dissimilar visual scenes are displayed (e.g., tablet); via a human-machine input (e.g., mouse) that causes a presentation of the input to be displayed over and concurrent with the first set of images; as markings made on printed material to which the dissimilar visual scenes is printed and shown; as verbal answers) from the person associated with the presented pattern of the first set of images as observed by the person; wherein presence and/or location and/or size of a gap or break in the observation of the presented pattern as ascertained from the captured input is used to assess the person's visual field.

In some embodiments, the first set of images are presented with temporal modulation (e.g., flicker-on and/or flicker-off for least than 30 msec, e.g., flicker-on for 333 msec and flicker-off for 500 msec) or with contrast modulation (e.g., a rate of 3 Hz).

In some embodiments, the first set of images are presented as a single static image.

In some embodiments, the target is placed in a location selected from the group consisting of a center field of the first set of images, a first corner field (e.g., upper-right field)

associated with a first quadrant of the first set of images, a second corner field (e.g., upper-left field) associated with a second quadrant of the first set of images, a third corner field (e.g., lower-left field) associated with a third quadrant of the first set of images, and a fourth corner field (e.g., lower-right field) associated with a fourth quadrant of the first set of images.

In some embodiments, stimulation of the dissimilar visual scenes is with a controlled vision device that provides separate visualization (e.g., isolated presentation) of the first set of images by the first eye and the second set of images by the second eye.

In some embodiments, the controlled vision device is selected from the group consisting of: a haploscopic device, a stereoscopic device; eyeglasses configured with one or more anaglyphic colored filters for use with an electronic display (e.g., projector display, desktop display, laptop display, tablet display, and mobile devices having sufficient screen size) or a printed material that are configured to appropriately display the first set of images and the second set of images as anaglyphic colored images; eyeglasses configured with one or more polarized filters for use with the electronic display or the printed material that are configured to appropriately display the first set of images and the second set of images as polarized images; a phase-haploscopic goggles (e.g., phase-haploscopic LC goggles, also referred to as LC shutter glasses and/or active shutter 3D glasses); a 3D virtual-reality head gear; and an augmented reality glass wear.

In some embodiments, the input comprises a graphical input received on an electronic human-machine-interface or on paper, wherein the graphical input is associated with edges of the gap or break in the observation of the presented pattern by the person.

In some embodiments, the input comprises a graphical or keyed input received on an electronic human-machine-interface or on paper, wherein the graphical or keyed input is associated with landmarks presented with (e.g., as an overlay) or on the first set of images, where identified landmarks are used to identify presence and/or location and/or size of a gap or break in the observation of the presented pattern.

In some embodiments, the captured input is directly received from the person.

In some embodiments, the captured input is indirectly received from the person through a technician (e.g., via verbal communication).

In some embodiments, the pattern having the one or more contour elements is continuously presented over an entirety of the first set of images.

In some embodiments, the assessment of the person's visual field is selected from the group consisting of: a sensitivity assessment of each of the first eye and the second eye; a pattern deviation index assessment; an assessment of difference in sensitivity between the first eye and the second eye; and a ratio assessment of the sensitivity between first eye and the summation of both eyes' sensitivity.

In some embodiments, the assessment of the person's visual field includes i) an assessment of visual field loss in one or both eyes of the person or ii) an assessment of visual defects in one or both eyes of the person.

In some embodiments, at least one of the first set of images is configured (e.g., in size and focal distance) to span at least 56 degrees of a horizontal field of view of a normal person and to span at least a 33 degrees of vertical field of view of a normal person.

In some embodiments, the pattern having one or more contour elements comprises a plurality of concentric circles.

In some embodiments, the pattern having one or more contour elements comprises a plurality of concentric circles including a circle selected from the group consisting of: a first concentric circle having a first radius corresponding to 1.5 degrees of a horizontal field of view of a normal person; a second concentric circle having a second radius corresponding to 10 degrees of a horizontal field of view of a normal person; a third concentric circle having a third radius corresponding to 17 degrees of a horizontal field of view of a normal person; a fourth concentric circle having a fourth radius corresponding to 25 degrees of a horizontal field of view of a normal person; a fifth concentric circle having a fifth radius corresponding to 40 degrees of a horizontal field of view of a normal person; a sixth concentric circle having a sixth radius corresponding to 60 degrees of a horizontal field of view of a normal person; and a seventh concentric circle having a seventh radius corresponding to 80 degrees of a horizontal field of view of a normal person.

In some embodiments, the pattern having one or more contour elements comprises a plurality of radial lines and one or more circles, wherein the plurality of radial lines and the one or more circles define identifiable landmarks to identify presence and/or location and/or size of a gap or break in the observation of the presented pattern.

In some embodiments, the method further includes determining (e.g., by a computer or by a person) one or more assessment of the person's visual field based on presence and/or location and/or size of a gap or break in the observation of the presented pattern as ascertained from the captured input.

In some embodiments, the method further includes generating, by the processor, a simulated visual-field loss stimulation within a pattern having the one or more contour elements of the first set of images, wherein the simulated visual-field loss stimulation are presented to at least one eye of the person; capturing one or more second inputs from the person associated with the presented visual-field loss stimulation as observed by the person; and determining, by the processor, one or more correlation values between the one or more second inputs and the presented visual-field loss stimulation, wherein the one or more correlation values are indicators of accuracy for the one or more second inputs, and wherein at least one of the one or more correlation values are used to stop or reject the measurement or assessment.

In some embodiments, the method further includes determining, by the processors, one or more eye positions of at least one eye of the person when the person is fixating on the target on the first set of images, wherein deviation of the determined eye position from an expected position of the eye is used to assess eye fixation accuracy or to terminate presentation of a portion of the dissimilar visual scenes.

In some embodiments, the method further includes, contemporaneous with the person fixating on a target on the first set of images, directly or indirectly capturing one or more third inputs from the person, wherein the capture is associated with an observed break at a left edge by a left eye (e.g., when viewing through a blue filter) or an observed break at a right edge by a right eye (e.g., when viewing through a blue filter).

In another aspect, a non-transitory computer readable medium is disclosed. The computer readable medium having instructions stored thereon, wherein execution of the instructions by a processor, cause the processor to perform any of the above processes.

In another aspect, a system is disclosed. The system includes a processor; and a memory having instructions stored thereon, wherein execution of the instructions by the processor causes the processor to perform any of the above processes.

BRIEF DESCRIPTION OF THE DRAWINGS

The patent or application file contains at least one drawing executed in color. This application is directed to evaluation of field of view of a person. Evaluative scenes and results, as presented in color, may be necessary for the understanding of the claims. Copies of this patent or patent application publication with color drawing(s) will be provided by the Office upon request and payment of the necessary fee.

The accompanying drawings, which are incorporated in and constitute a part of this specification, illustrate embodiments and together with the description, serve to explain the principles of the methods and systems. Embodiments of the present invention may be better understood from the following detailed description when read in conjunction with the accompanying drawings. Such embodiments, which are for illustrative purposes only, depict novel and non-obvious aspects of the invention. The drawings include the following figures.

FIG. 1 shows a system for contemporaneously and concurrently presenting dissimilar visual scenes to a person to stimulate both eyes for the assessment of visual field of the person in accordance with an illustrative embodiment.

FIG. 2A and FIG. 2B show an example of dissimilar visual scenes that can be used to stimulate both eyes in which FIG. 2A shows an example image having a pattern that is rich in contours and FIG. 2B shows an example image that is impoverished with respect to the first image, in accordance with an illustrative embodiment.

FIG. 12 shows a table of results for four patients assessed using the exemplified methods and systems, in accordance with an illustrative embodiment.

FIG. 26 shows experimental results of the BVF mapping based on smaller sizes test stimuli and same BVF mapping superimposed over HVF mapping, in accordance with an illustrative embodiment.

DETAILED SPECIFICATION

Figure 2A:
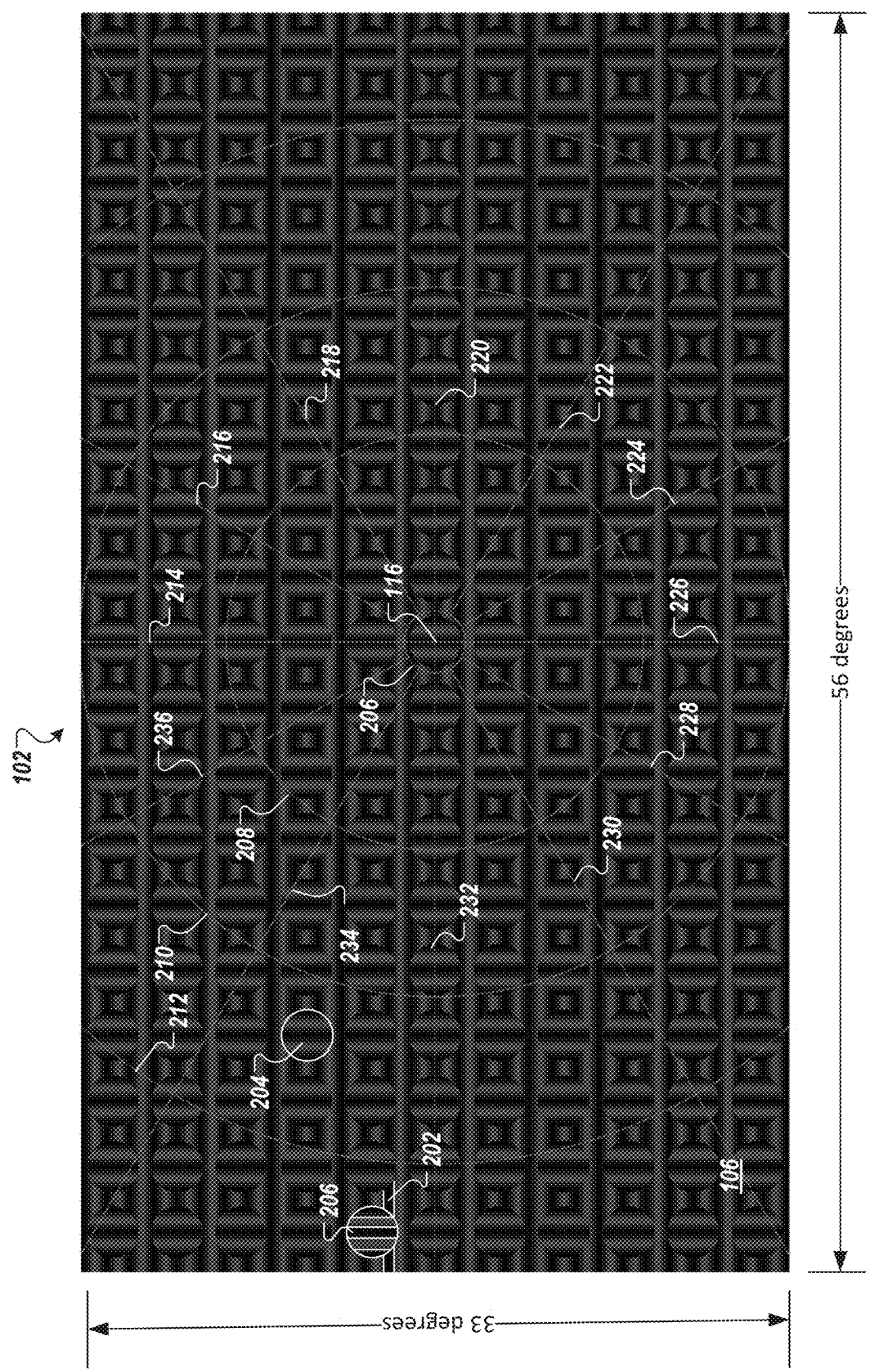

Each and every feature described herein, and each and every combination of two or more of such features, is included within the scope of the present invention provided that the features included in such a combination are not mutually inconsistent.

FIG. 1 shows a system 100 for contemporaneously and concurrently presenting dissimilar visual scenes to a person to stimulate both eyes for the assessment of the visual field of the person in accordance with an illustrative embodiment. As shown in FIG. 1, the dissimilar visual scenes includes a first image 102 having a pattern 106 that substantially spans across the image and is rich in contours (e.g., a scene with rich texture patterns) to stimulate the first eye 108 (shown as the left eye 108) and a second image 104 that is impoverished with respect to contour elements of the first image 102 to stimulate the second eye 110 (shown as the right eye 110). Each of the presented images (102, 104) spans a respective visual field 112 of a person for a given eye. In some embodiments, the first image 102 has a first pattern 106 and the second image is a background image without any pattern. In other embodiments, each of first image 102 and the second image 106 has contour patterns 106 but the contour pattern of the first image 102 is orthogonal to the contour pattern of the second image 106.

During an assessment, the person fixates at a target 116 located on the image 102 that corresponds to one or more fixation points 118 in the visual field and provides input associated with a perceived or observed "break" in the pattern (i.e. an area without distinguishing contours). A visual field defect is assessed to be present in, or associated with, the eye under test (i.e., the eye presented with the image 102 having the pattern 106) if the person observes a portion of the scene viewed by the other eye (i.e., eye not being tested with image 104) and/or if the person sees a gap or break in the pattern 106 that is presented to the eye under test. The dissimilar visual scenes are then switched, in some embodiments, between the two eyes to test the other eye in which image 102 (with the contour-rich scene) is presented to the second eye 110, and image 104 (with the impoverish scene or dissimilar scene) is presented to the first eye 108. As used herein, the term "image" refers to a single instance of presentation of visual information that is observed by a person and can be a static image or a frame from a sequence of images.

Figure 2B:
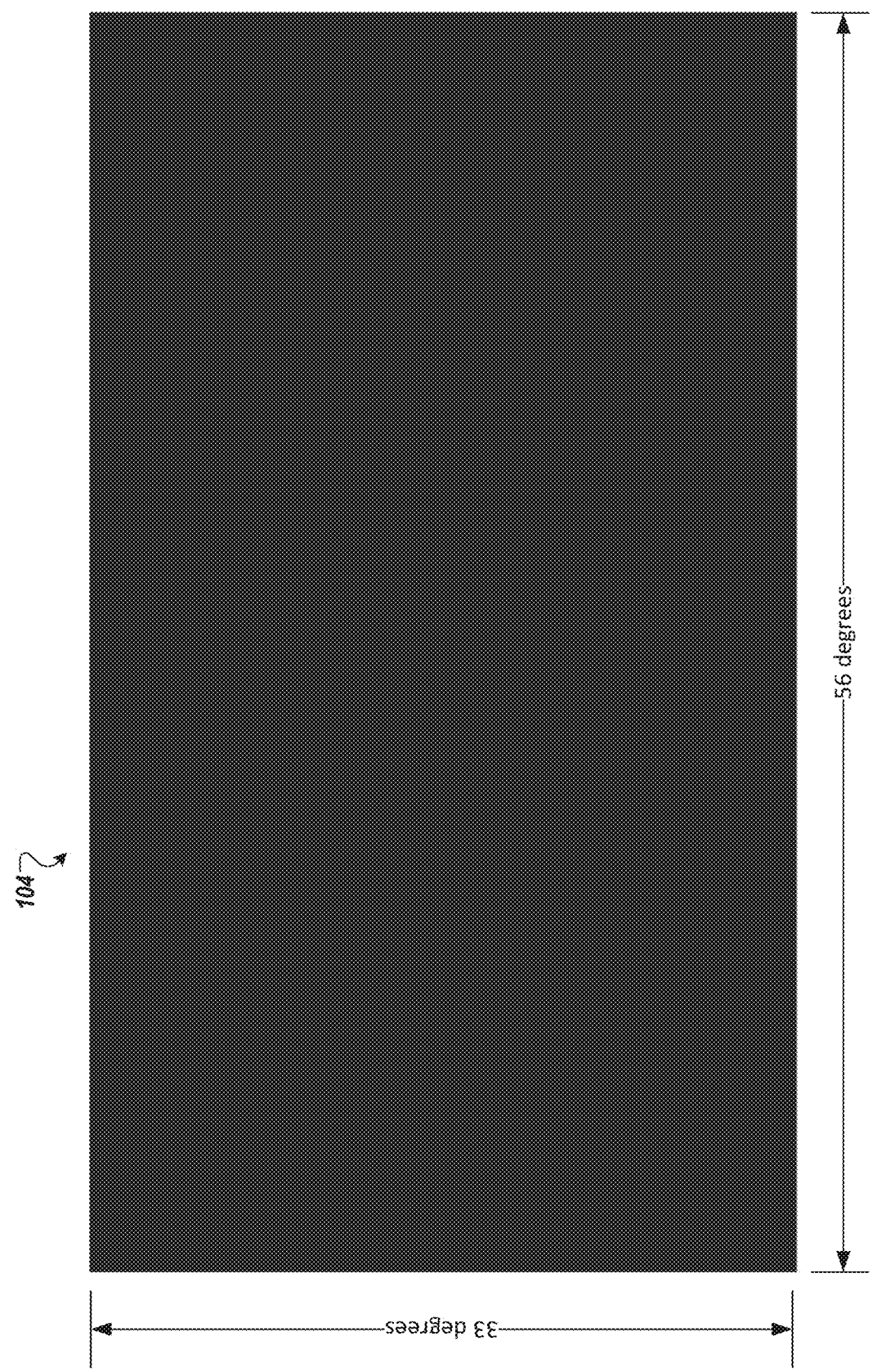

FIG. 2A and FIG. 2B show an example of dissimilar visual scenes that can be used to stimulate both eyes in which FIG. 2A shows an example image 102 having a pattern 106 that is rich in contours and FIG. 2B shows an example image 104 that is impoverished with respect to the first image 102, in accordance with an illustrative embodiment.

As shown in FIG. 2A and FIG. 2B, each of the images 102, 104 is configured to be presented along a visual field having a horizontal span of about 56 degrees and a vertical span of about 33 degrees. To this end, each of the images 102, 104 substantially spans the visual field of each of the eye that is commonly tested in the clinical setting.

As shown in FIG. 2A, the pattern 106 is formed from a plurality of observable horizontal lines 202 (shown with highlighted horizontal lines for emphasis) that are superimposed by observable circular overlays 204 (shown with a highlighted circle for emphasis) having a different periodicity to the horizontal lines 202, wherein each circular element 204 shows a same set of observable vertical lines 206 (shown with highlighted vertical lines for emphasis).

Other types of texture patterns can be used—examples can include a set of observable radial gratings and/or lines. Also, the observable texture can be structured (as shown) or non-structured (e.g., have the appearance of random). In various embodiments, the observable contours that make up the texture pattern substantially cover (e.g., having greater than 80%) the presented scene. As shown in FIG. 2A, the texture pattern completely spans the presented scene.

In FIG. 2A, the image 102 also includes concentric circles 206, 208, 210, and 212 superimposed on the pattern 106. The concentric circles 206, 208, 210, and 212 are concentric to the target 116 defined by circle 206. Further, in FIG. 2, the image 102 also includes 12 radial lines 214-236 (corresponding to clock hour hands) that are co-centered to the concentric circles 206, 208, 210, and 212. The concentric circles 206-212 and radial lines 214-236 can serve as landmarks to help in the localization of defects by a subject (i.e., identify location of breaks or discontinuity in the image 102). A technician conducting the test can, for example, use the landmarks to readily gauge locations of a person's visual-field defects.

As shown, the radii of the concentric circles 206, 208, 210, and 212 are located at about 1.5 degrees, 10 degrees, 17 degrees, and 25 degrees of the horizontal or vertical field. Other number (including zero) and location of concentric circles can be used for the purpose of serving as landmarks or as part of the pattern. Also, other number (including zero) and radial location of radial lines can be used.

FIG. 2B shows an example image 104 that is impoverished with respect to the first image 102. In this example, the example image 104 is completely homogeneous and is without any observable contour features. That is, the example 104 of FIG. 2B is shown as a colored field.

In some embodiments in which the impoverished image 104 includes a homogenous background, the stimulus color of the image 104 can be any color that allows a person to readily discriminate or contrast with the contour-rich image 102. Where anaglyphic filters (i.e., having different color filters) are used, the images 102, 104 are configured with colors that are substantially non-overlapping in spectral color (e.g., red and blue; red and green; magenta and green; etc.).

However, in some embodiments, observable contour features can be visually included in image 104. For example, the image 104 can have a substantially similar or same grating lines as the corresponding image with the rich contours, in which the observable texture of the impoverished image 104 has a subset of observable distinguishing contours of the image 102.

As noted above, each of the presented images (102, 104) substantially spans (e.g., greater than 25%) a respective visual field of a person for a given eye. A visual field of a single eye for an average person typically extends nasally about 60 degrees (i.e., toward the nose, or inward) from a vertical meridian in each eye and extends temporally about 107 degrees (i.e., away from the nose, or outwards) from that vertical meridian. The visual field also extends about 70 degrees above and about 80 degrees below a horizontal meridian. Visual field loss may occur due to disease or disorders of the eye (e.g., shown as 108, 110), optic nerve (e.g., shown as 120), or brain. These visual field loss can include altitudinal field defects—which involves loss of vision above or below the horizontal and is associated with ocular abnormalities; bitemporal hemianopia—which involves a loss of field of vision at the side portions of the field; central scotoma—which involves a loss of central vision; and homonymous hemianopia—which involves a loss at one side of the visual field for both eyes, e.g., due to defects located behind the optic chiasm. Multiple embodiments of different image sizes are provided herein to assess different degree of coverage over the visual field. Larger screens can be used to test larger portions of the visual field.

Figure 3:
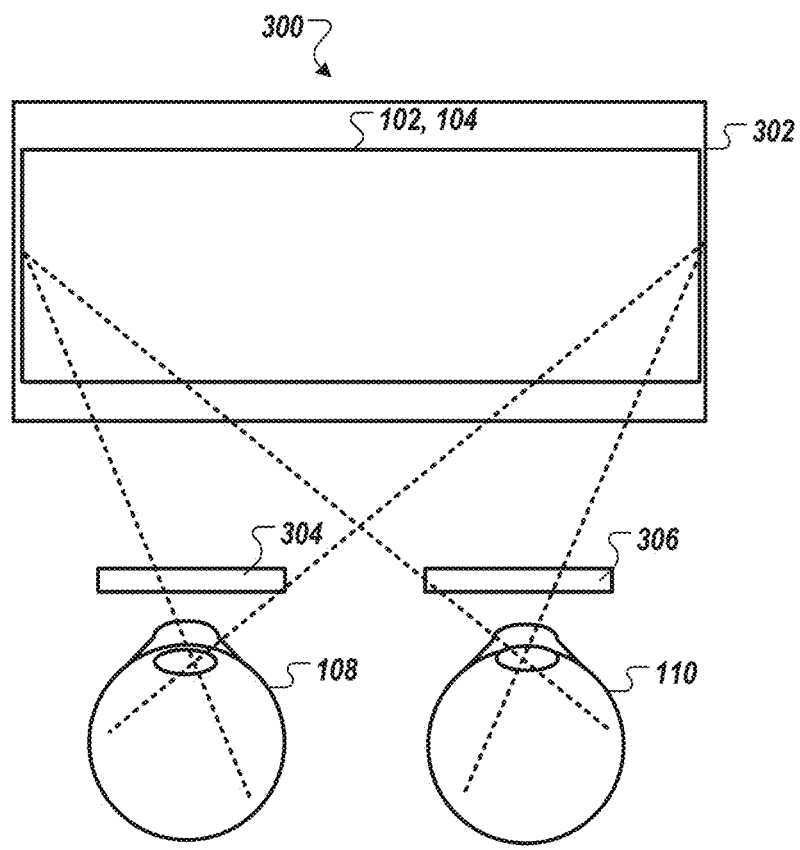
FIG. 3 and FIG. 4 each shows an embodiment of a system to measure and/or assess a person's visual field in accordance with an illustrative embodiment.
Figure 4:
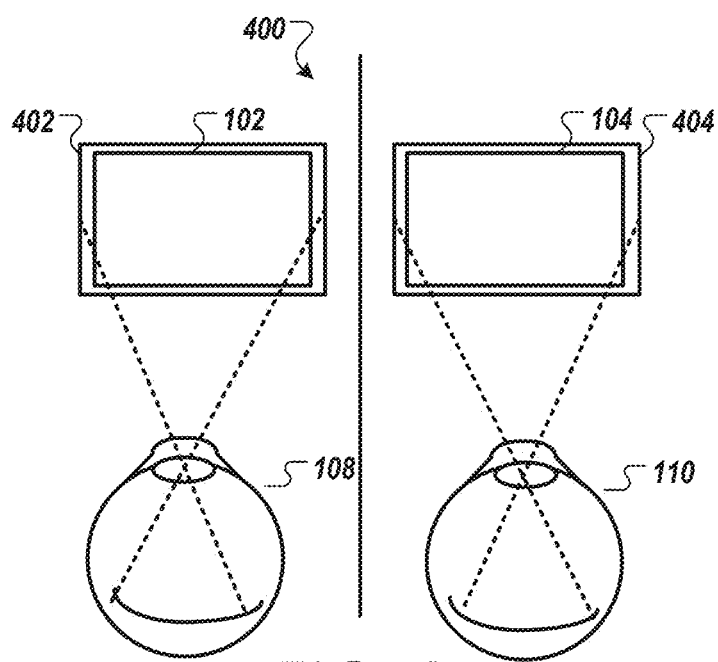

FIG. 3 and FIG. 4 each shows an embodiment of a system to measure and/or assess a person's visual field in accordance with an illustrative embodiment. In FIG. 3, the system 300 includes a single visual source 302 (e.g., an electronic display or a printed material), and the two eyes (108, 110) are allowed to view different image scenes (e.g., 102, 104) by use of optical filters 304, 306 that allows only respective images (e.g., 102, 104) of the different image scenes to be observed by each of the eye (108, 110) (i.e., when both eyes are open). In some embodiments, the optical filters 304, 306 include color filter glass elements (e.g., to form an anaglyph or stereoscopic device). In other embodiments, the optical filters 304, 306 include polarizing filter glass elements. Other types of optical filters such as a phase-haploscopic goggles (e.g., phase-haploscopic LC goggles) can be used so as to allow separate visual scenes to be presented to the two eyes (108, 110). The visual source 302 is configured to output each scenes of the dissimilar visual scenes according to the configuration of the optical filters 304, 306. The visual source 302 may be a projector display, a desktop display, a laptop display, a tablet display, and a display mobile device that can be adapted to span a substantial portion of a person's visual field with sufficient contrast or display resolution.

In FIG. 4, the system 400 includes two independent display outputs 402, 404 to provide the dissimilar visual scenes to each of the two eyes (108, 110). The two independent display outputs 402, 404 may be part of a haploscopic device, a stereoscopic device, a 3D virtual-reality head gear, or an augmented reality glass wear.

The exemplified systems and methods can be used to detect visual field loss quickly as multiple portions of the visual field are tested simultaneously across the presented test image. In many instances, we observed that a person can view and provide feedback on the entire presented test image in seconds for each eye under test as compared to conventional techniques, which often takes about 10-15 minutes to perform. We further observed that test results of the exemplified systems and methods are not affected by eye movements, and visual-field defects can be detected irrespective of eye position. Thus, less complex hardware as well as less complicated test procedures (as compared to conventional techniques of visual field) can be used.

Further, in addition to being used by trained professionals in dedicated medical settings, the exemplified systems and methods facilitates assessment and/or measurement of visual-field defects by lay persons to screen for visual-field defects and to monitor eye-disease state and progression of such disease state during treatment. The system can be made very portable to allow tests at home and at various locations where assessment of visual-field defects is desired (for example, at nursing home, local drug stores, sport events and arenas).

FIGS. 5A, 5B, 6A, 6B show two sets of example dissimilar visual scenes that can be used to stimulate the eyes, in accordance with an illustrative embodiment.

Figure 5A:
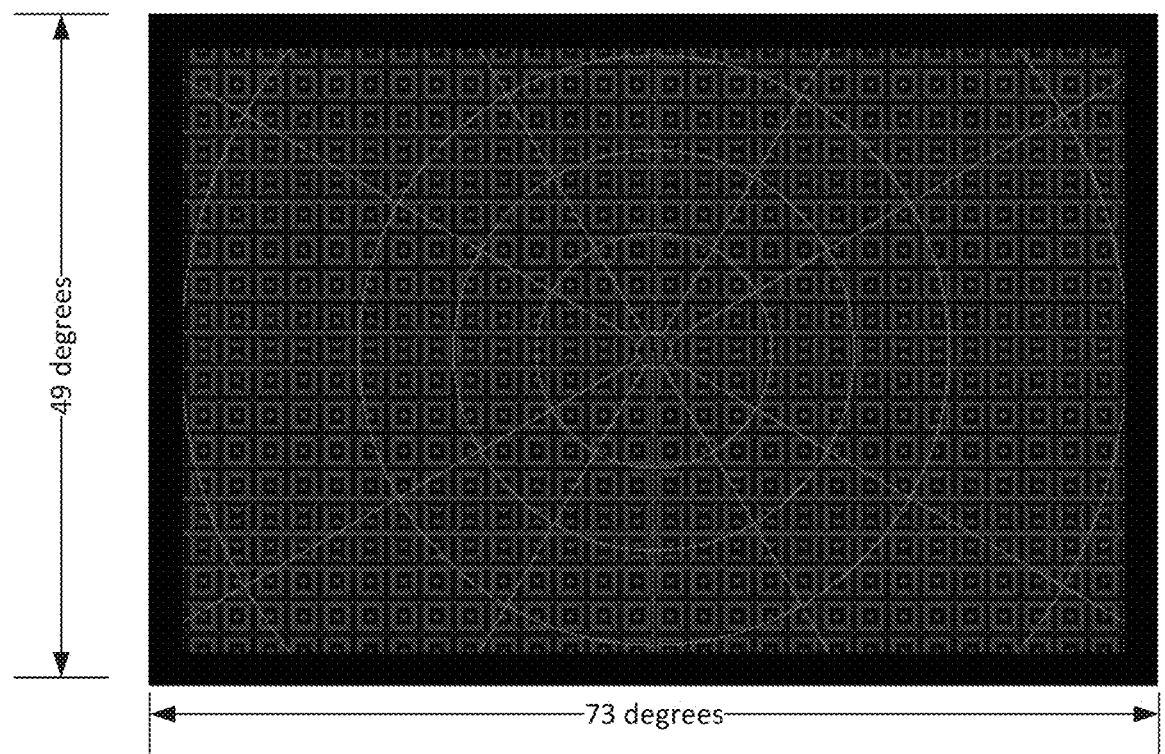
FIGS. 5A, 5B and FIGS. 6A, 6B show two respective sets of example dissimilar visual scenes that can be used to stimulate the eyes, in accordance with an illustrative embodiment.
Figure 5B:
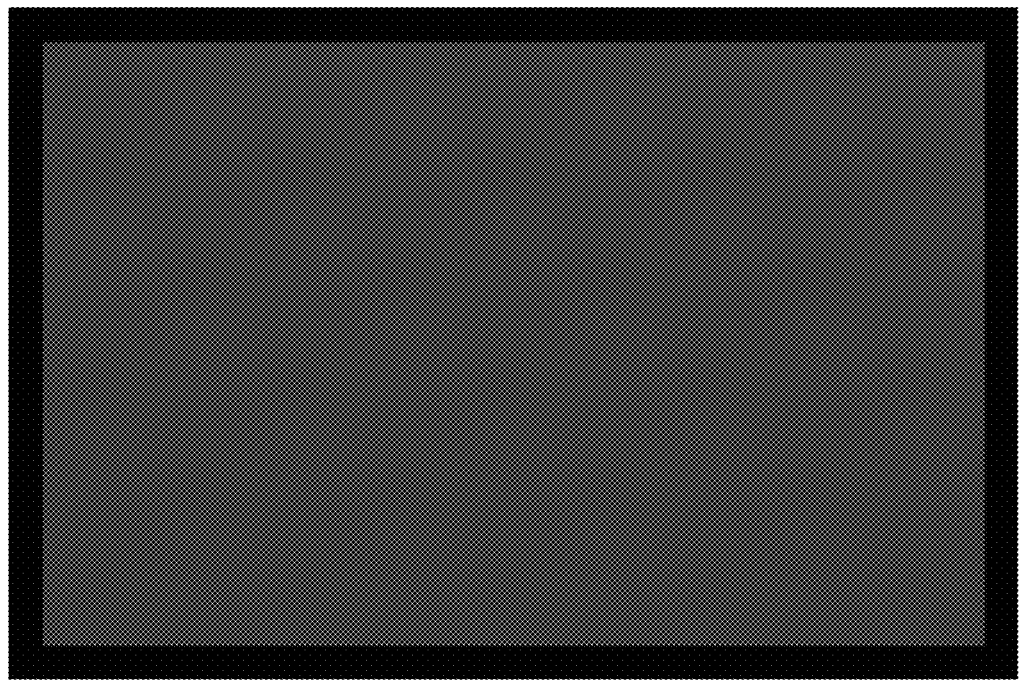
Figure 6A:
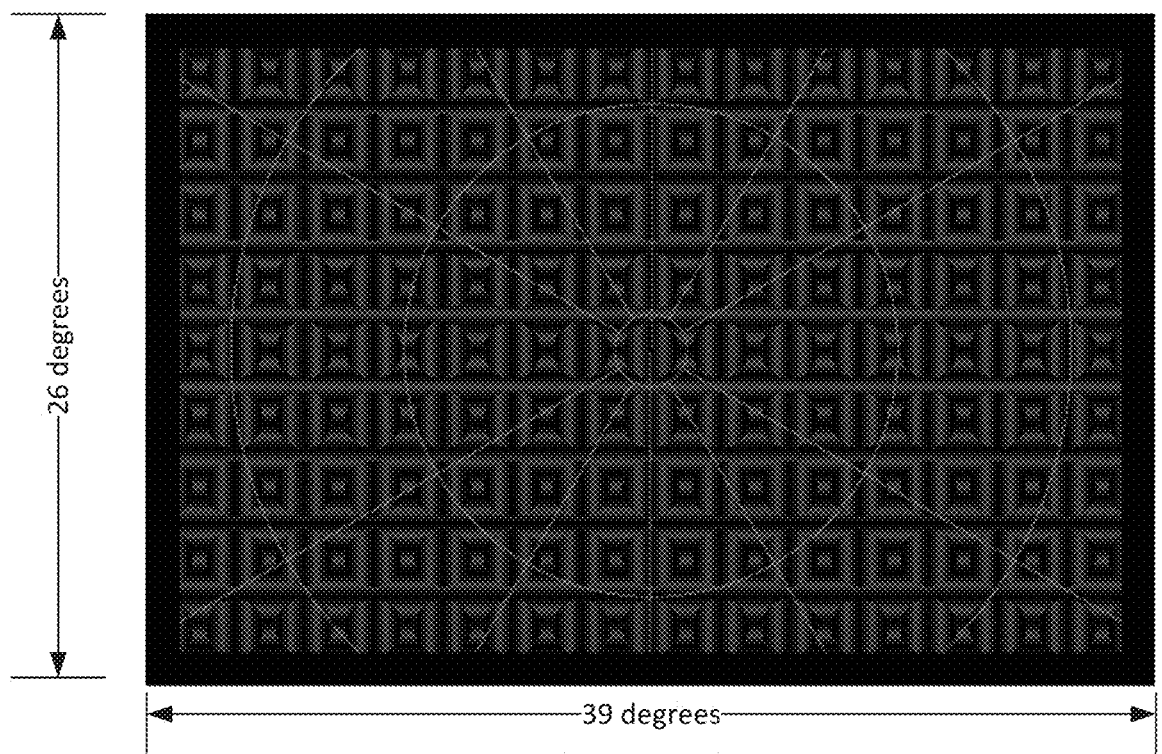
Figure 6B:
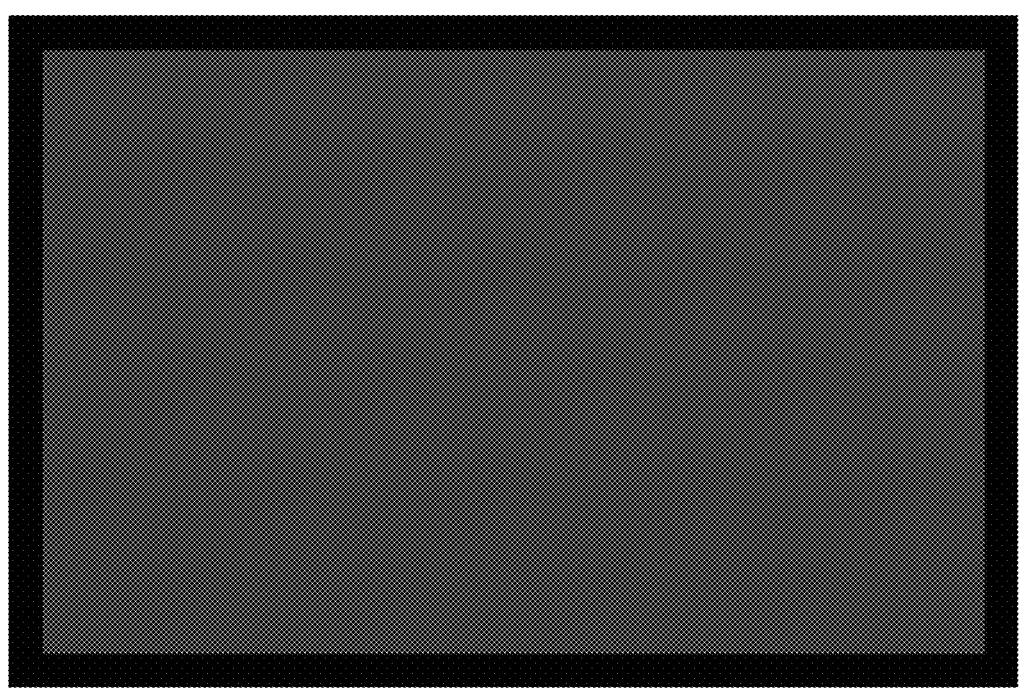

As shown in FIGS. 5A-5B and 6A-6B, each of the images 102, 104 also substantially spans the visual field (as in FIGS. 2A and 2B) of each of the eyes of an average person. In FIG. 2A and FIG. 2B, each of the images 102, 104 has a horizontal field span of about 56 degrees and a vertical field span of about 33 degrees. In FIG. 5A and FIG. 5B, each of the images 102, 104 has a larger horizontal field span of about 73 degrees and a larger vertical field span of about 49 degrees. In FIG. 6A and FIG. 6B, each of the images 102, 104 has a horizontal field span of about 39 degrees and a vertical field span of about 26 degrees. The images 102, 104 of FIGS. 2A-2B, 5A-5B, and 6A-6B can be produced, for example, on a display area at least 27 inches and, for example, visualization in conjunction with a stereoscopic glasses. Other display sizes, e.g., those of handheld devices, can be used if they sufficiently cover the visual field of a person (e.g., a smart-phone coupled to a headgear). Other field span can be used depending on the screen size of the test device.

Though the images 102, 104 are shown with boundaries that are characterized as being rectangular, other image shapes can be used. In some embodiments, the images can have boundaries that are characterized as being circular. In some embodiments, the images can have boundaries that are characterized as being oval.

FIGS. 7A, 7B, 7C, 7D and FIGS. 8A, 8B, 8C, and 8D show two respective sets of image 102 having a non-center fixation target that can be used to stimulate the eyes, in accordance with an illustrative embodiment.

Figure 7A:
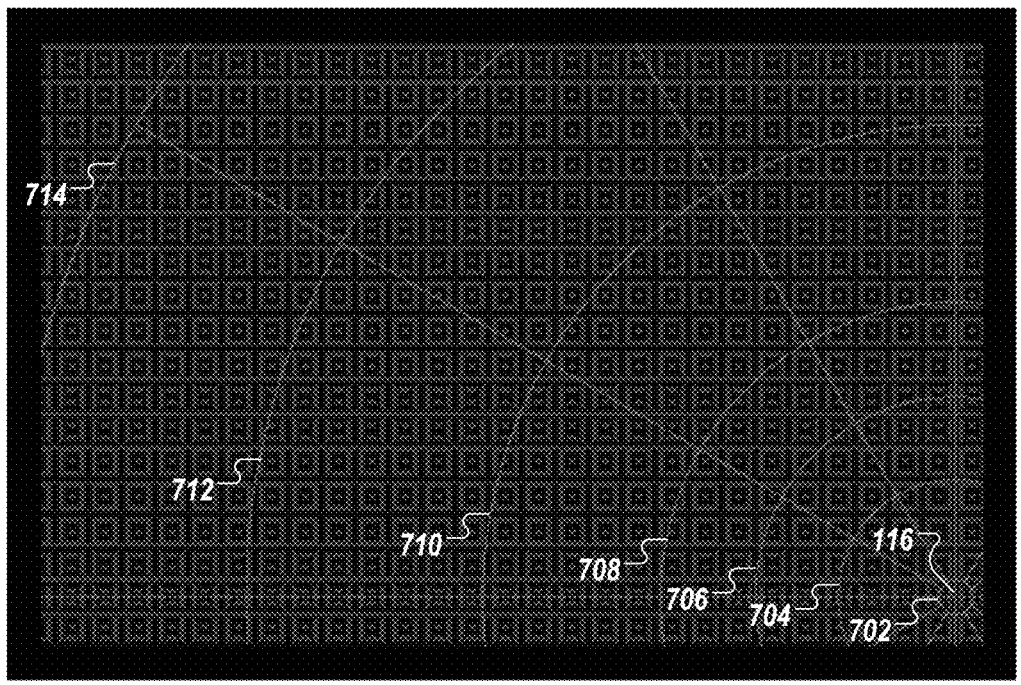
FIGS. 7A, 7B, 7C, 7D and FIGS. 8A, 8B, 8C, and 8D show two respective sets of example dissimilar visual scenes having a non-center fixation target that can be used to stimulate the eyes, in accordance with an illustrative embodiment.
Figure 7B:
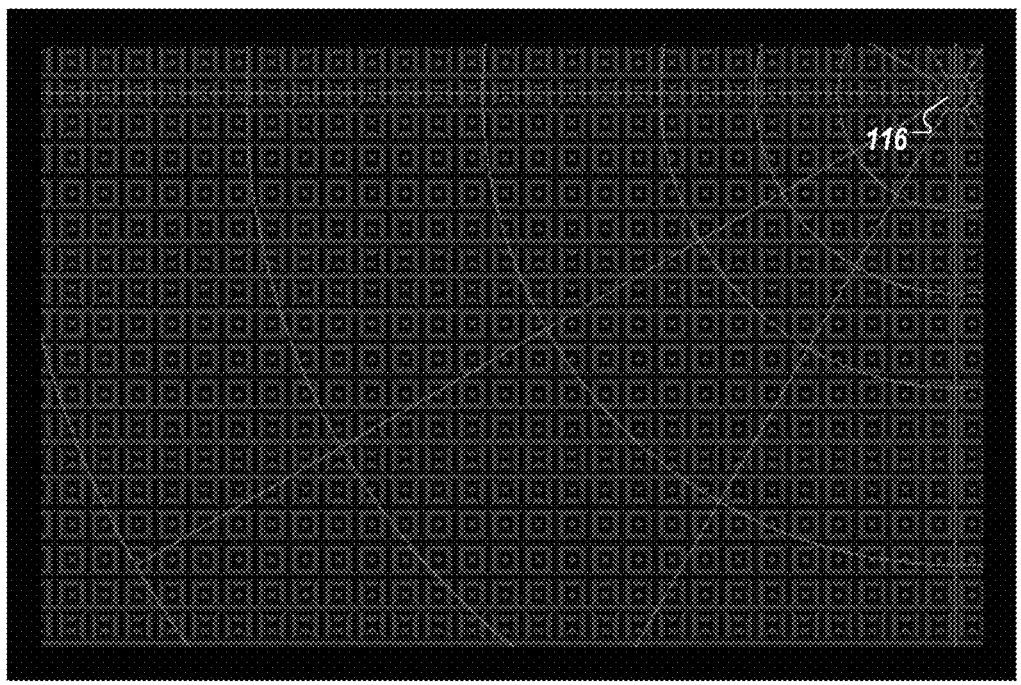
Figure 7C:
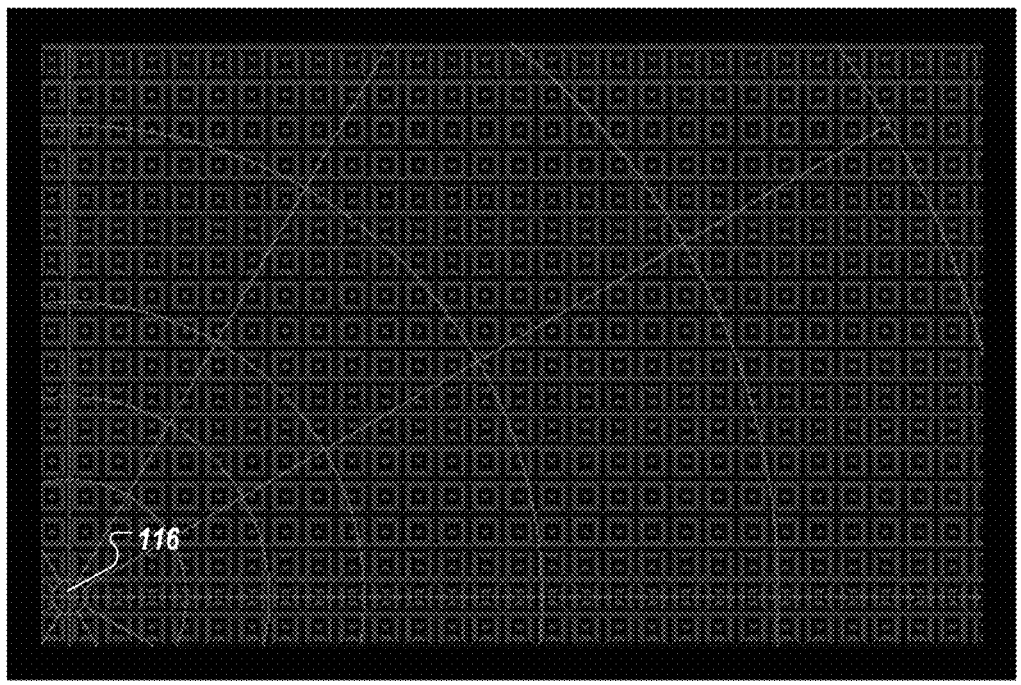
Figure 7D:
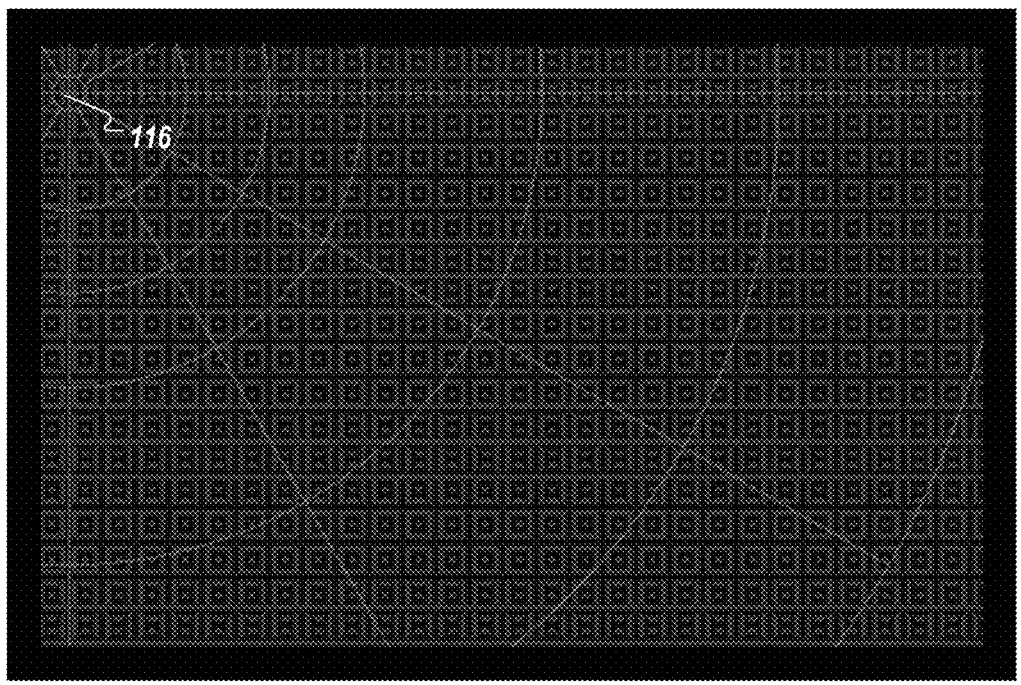

In FIGS. 7A-7D, the fixation target 116 is shown at, or near, each of the corner of the four quadrants. The visualization of FIGS. 7A-7D corresponds to that of FIG. 5A (which shows a center fixation target). In FIGS. 7A, the radii of the concentric circles are located at about 1.5 degrees (arrow 702), about 10 degrees (arrow 704), about 17 degrees (arrow 706), about 25 degrees (arrow 708), about 40 degrees (arrow 710), about 60 degrees (arrow 712), and about 80 degrees (arrow 714) of the horizontal or vertical field. Corresponding radii of the concentric circles are shown at same radii location in FIGS. 7B, 7C, and 7D.

Figure 8A:
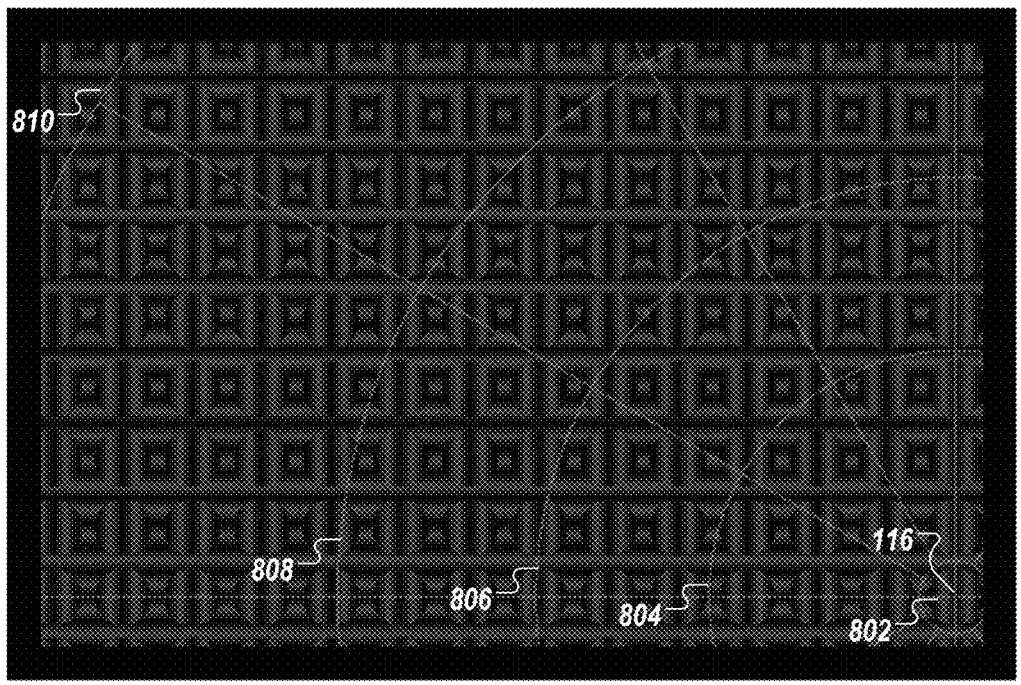
Figure 8B:
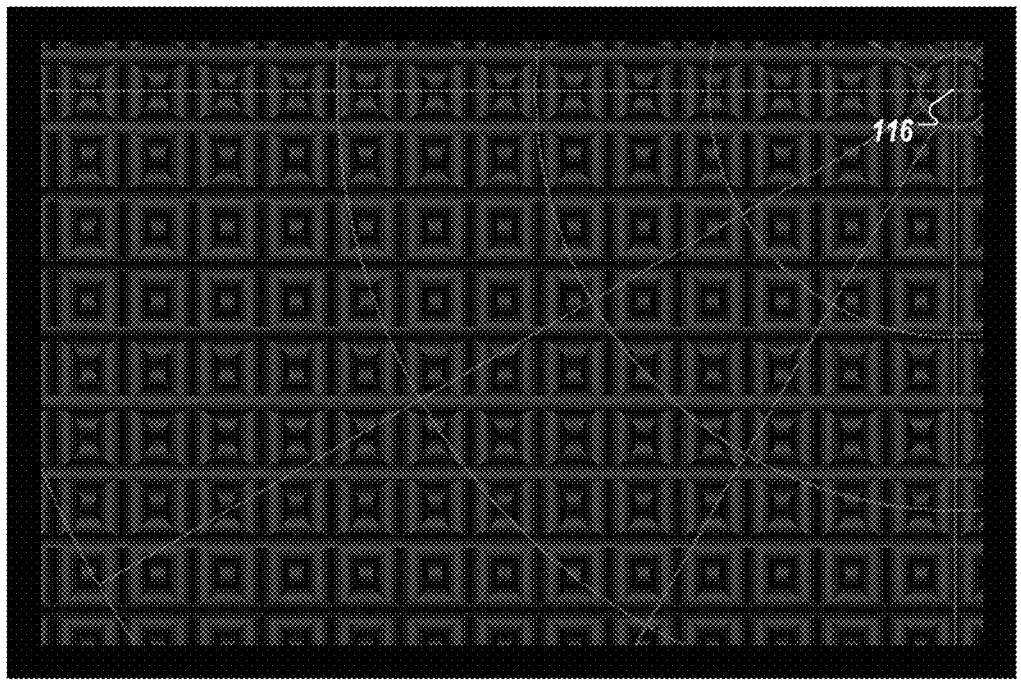
Figure 8C:
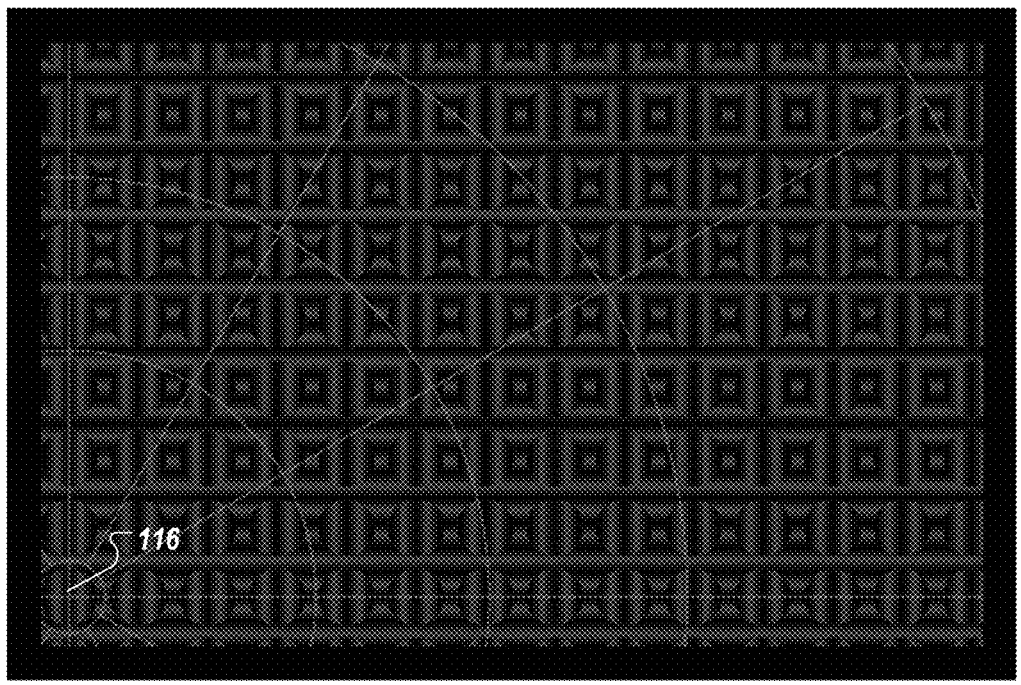
Figure 8D:
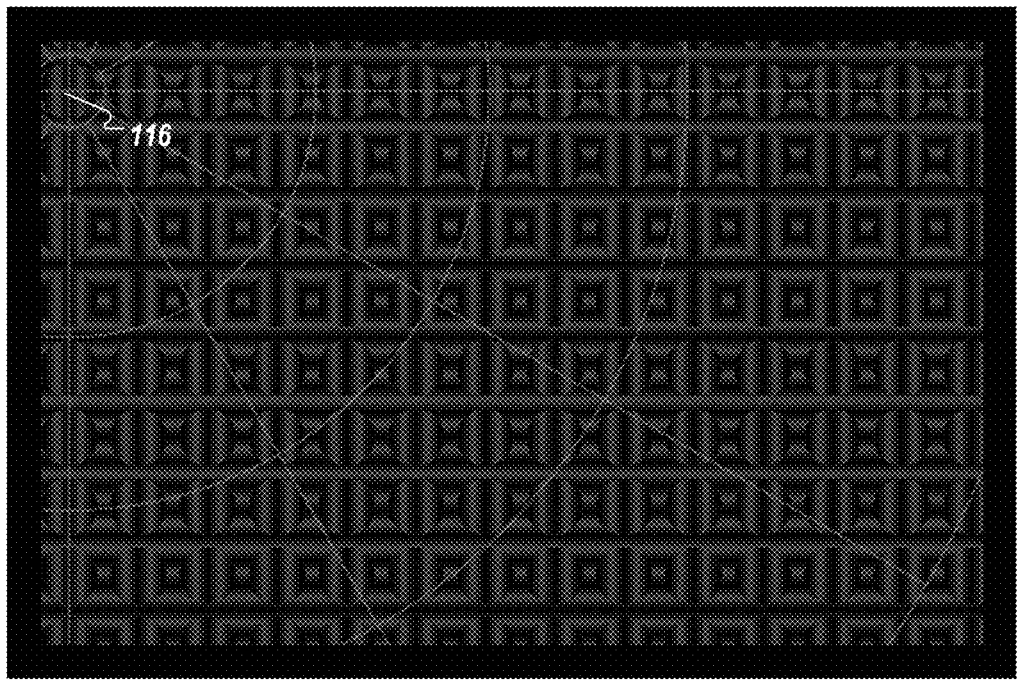

In FIGS. 8A-8D, the fixation target 116 is shown at, or near, each of the corner of the four quadrants. The visualization of FIGS. 8A-8D corresponds to that of FIG. 6A (which shows a center fixation target). In FIGS. 8A, the radii of the concentric circles are located at about 1.5 degrees (arrow 802), about 10 degrees (arrow 804), about 17 degrees (arrow 806), about 25 degrees (arrow 808), and about 40 degrees (arrow 810). Corresponding radii of the concentric circles are shown at same radii location in FIGS. 8B, 8C, and 8D.

In another aspect, rather than a static image, the images of the dissimilar visual scenes can be modulated or varied in time, space, contrast, etc. In some embodiments, a first set of images corresponding to the contour-rich image 102 are presented.

In some embodiments, the images of 102 of FIGS. 2A, 5A, 6A can be temporally modulated. For example, the image can have an "on" duration cycle of about 333 msec and an "off" duration cycle of about 500 msec. Other "on" and "off" duration cycle can be used where the "on" and/or "off" duration cycle is greater than 30 msec.

Figure 9A:
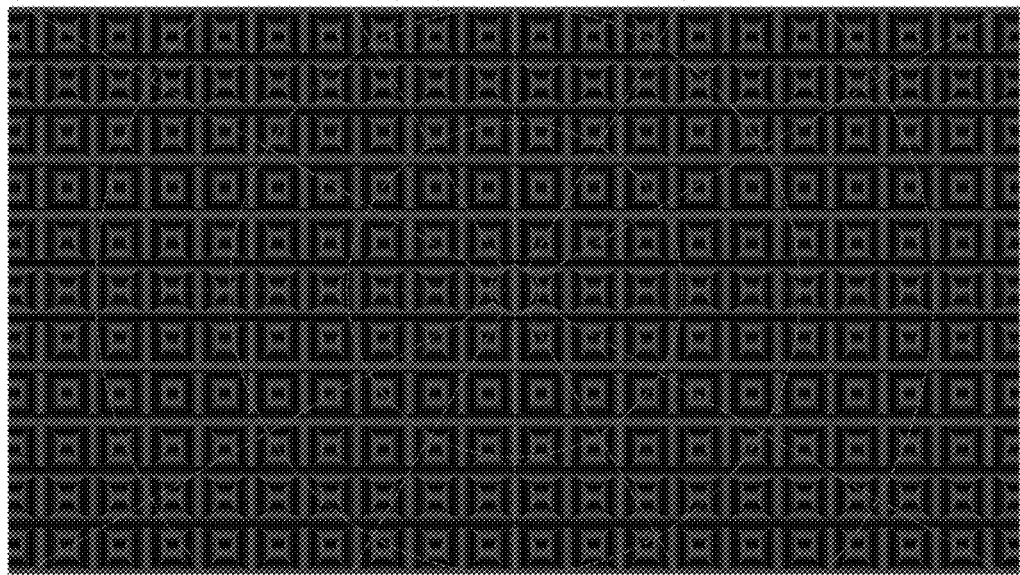
FIGS. 9A, 9B, 9C, 9D, 9E, 9F, 9G, and 9H show an example set of image of FIG. 2A that can be modulated with varying contrast of a same base image, in accordance with an illustrative embodiment.
Figure 9B:
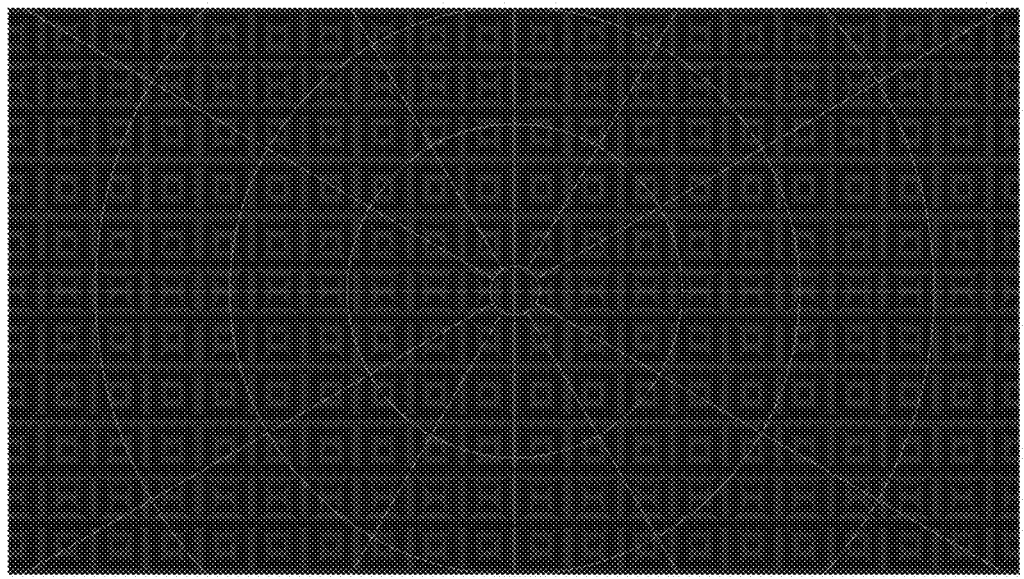
Figure 9C:
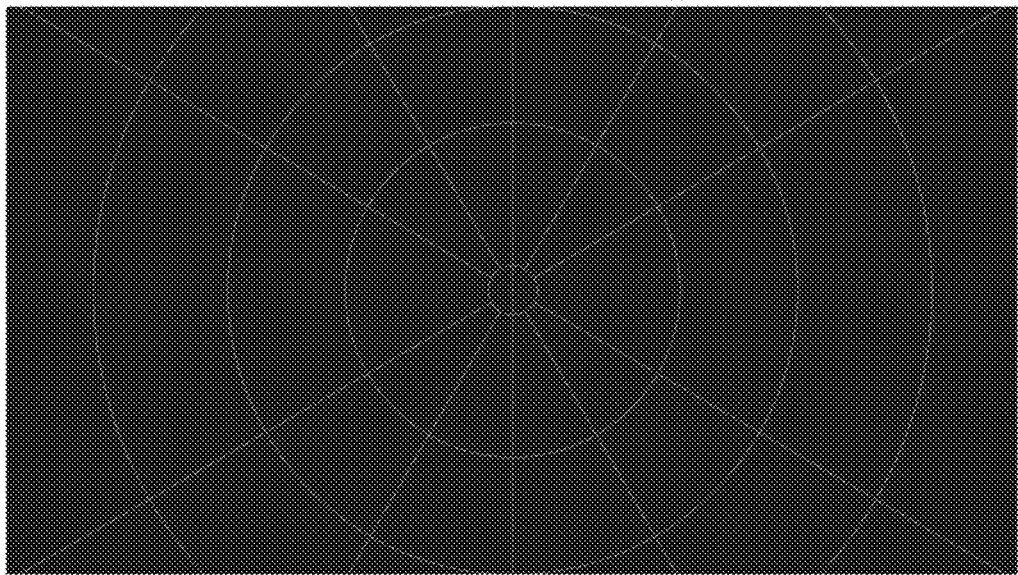
Figure 9D:
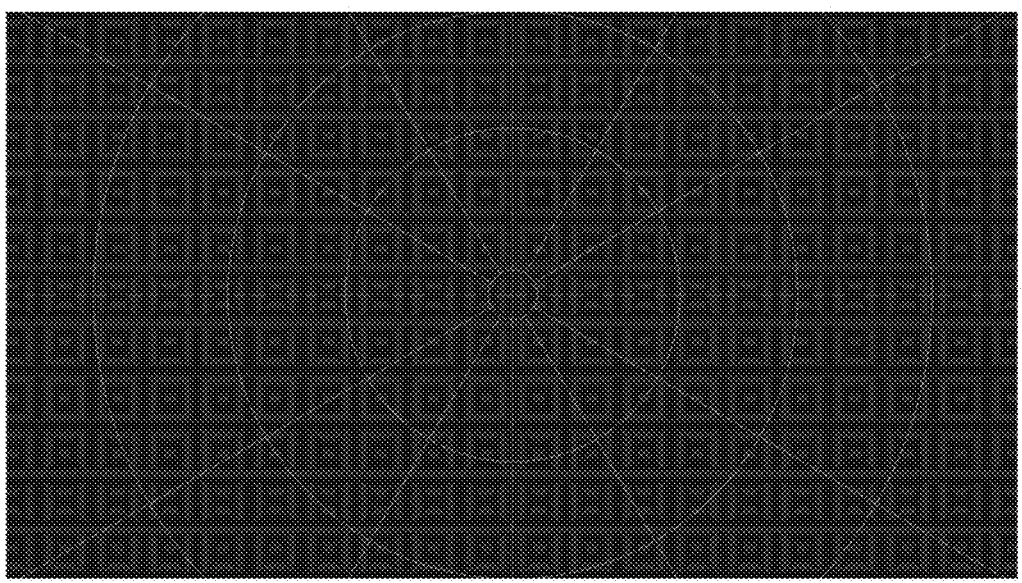
Figure 9E:
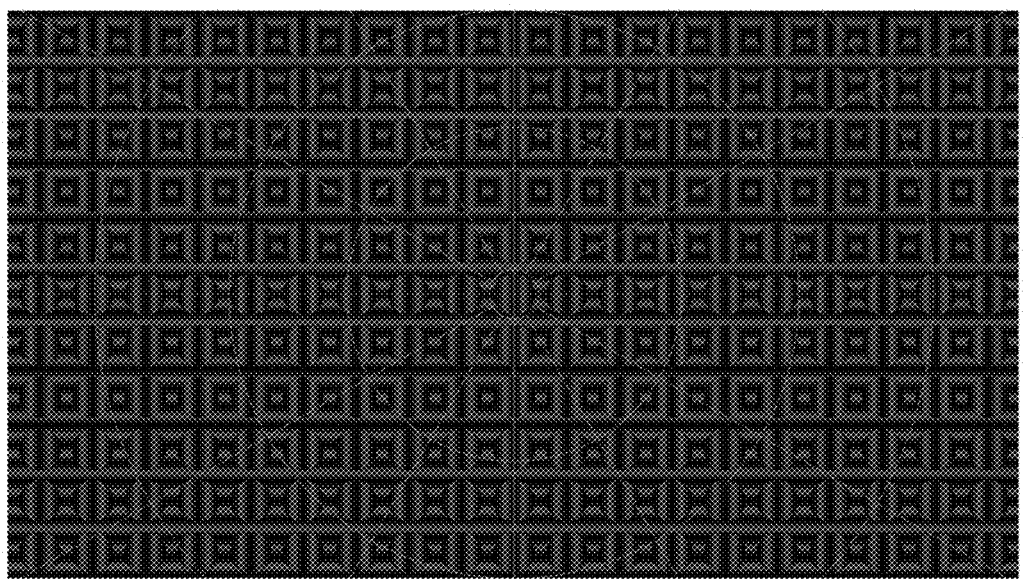
Figure 9F:
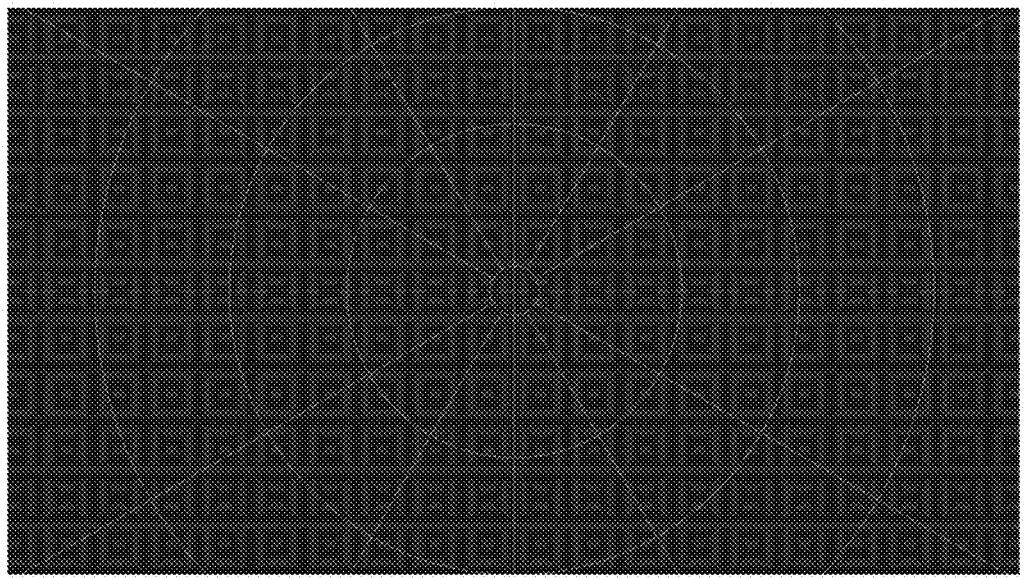
Figure 9G:
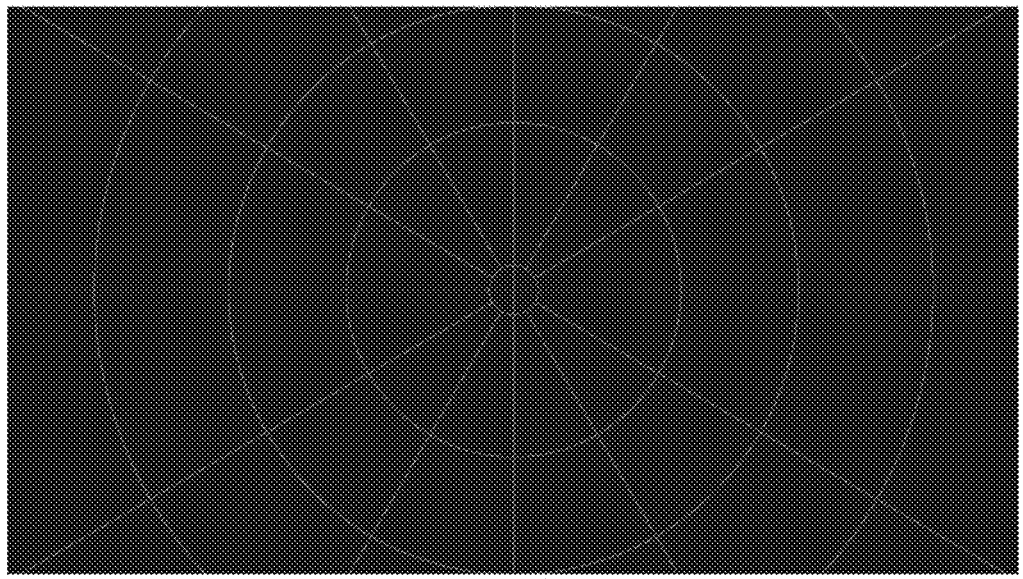
Figure 9H:
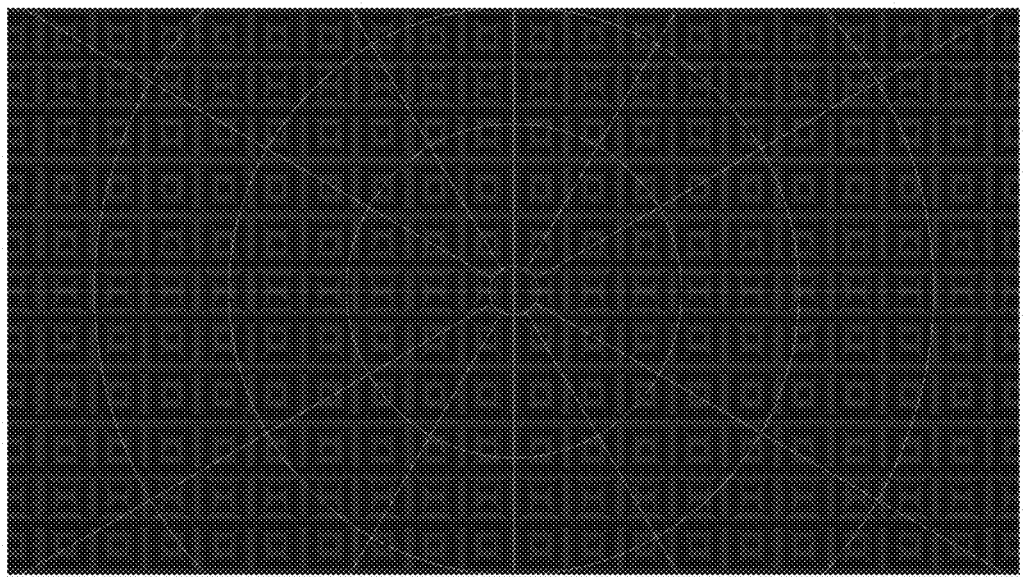

FIGS. 9A, 9B, 9C, 9D, 9E, 9F, 9G, and 9H show an example set of images of FIG. 2 that are modulated with varying contrast of a same base image, in accordance with an illustrative embodiment. As shown, the pattern portion of the image 102 is varied in contrast (while contrast of the radii lines and the radial lines are fixed) across contrast values of −1.0, −0.5, 0.0, 0.5, and 1.0. As shown, FIG. 9A has a contrast value of 1.0; FIG. 9B has a contrast value of 0.5; FIG. 9C has a contrast value of 0.0; FIG. 9D has a contrast value of −0.5; FIG. 9E has a contrast value of −1.0; FIG. 9F has a contrast value of −0.5, FIG. 9G has a contrast value of 0.0; and FIG. 9H has a contrast value of 0.5. The set of images can be modulated at a rate of 3 Hz. Other numbers of images and modulation rates can be used.

Other type of modulation, e.g., via an animation sequence, may be used. In some embodiments, the pattern may be varied spatially. In other embodiments, the fixation target may be varied spatially.

Assessment of Visual-Field Defect

In another aspect, the exemplified systems and methods involve the capture (direct or indirect) of one or more inputs, from the person being tested, associated with the presented pattern so as to identify presence and/or location and/or size of a gap or break in the observation of the presented pattern as ascertained from the captured input. The input is captured contemporaneous from the person under test being stimulated with the dissimilar visual scenes. As used herein, the term "contemporaneous" refers to the events being concurrent with one another as well as to events that occur in proximal to or immediately after another event. To this end, the input can be captured while the person is being stimulated and the input can be captured immediately after (in which the person is providing recollection of gaps or breaks in the observation of the presented pattern from his or her memory).

Referring back to FIG. 1, the system 100 is configured with a hand-held pointing device 122 that directly or indirectly receives input from the person under test. In some embodiments, the input is directly received from the person under test who uses the hand-held pointing device to draw on the image 102. In other embodiments, the input is indirectly received from the person under test who instructs a user (e.g., a technician) to use the hand-held pointing device to draw on, or to record such inputs, on the image 102.

In some embodiments, the input of the hand-held pointing device 122 is concurrently presented on, or along with, the image 102. In some embodiments, the presentation of the input with, or over, the image 102 can be in the form of lines that distinguishes from the presented pattern 106 and/or concentric and radial lines.

Discussion

Without wishing to be bound to a particular theory, the exemplified systems and methods are based on the mechanism of interocular suppression. The images are designed such that for normal vision, the tested-eye viewing the textured pattern will dominate while the non-tested eye (with homogeneous image) will be suppressed. This leads to the subject seeing the textured pattern. This methodology can be referred to as the binocular visual field of inhibition ("BVF").

It is noted that if a particular location of the visual field in the non-tested eye is more sensitive than the eye being tested (which can be due to a loss/defect of visual field in the corresponding location of the tested-eye), then that location (area) in the non-tested eye will be seen as dominant. This can lead to the subject seeing a break in the texture pattern. The area size and location of the break correspond approximately to a deficit in the tested eye. The area size and location of the captured input could be shifted in instances when the subject is providing the input while not directly looking at the capture device. However, this variability does not invalidate the diagnostic result of the test as a break in the texture pattern has still been observed indicating presence of a defect.

Experimental Results and Examples

A first proof-of-concept evaluation comprising a set of comparative test of subjects using the exemplified systems and methods (referred to herein as the exemplary visual test) and the HVF instrument and method had been conducted. Results of these two distinct tests are combined and concurrently presented in a same result output. It is observed that there is a clear overlap between results acquired and assessed via the exemplified systems and methods and a corresponding Humphrey visual field analysis.

During the experiment, a subject's visual-field defect is first measured using the HVF instrument. The subject's visual-field defect is then measured using the exemplified systems and methods. Because Humphrey's visual field analysis only tests the visual field at every 6-degrees of spatial interval and is based on a monocular measurement, Humphrey's visual field-based data are superimposed at every 6-degree spatial intervals over the continuously tested field results of the exemplified systems and methods.

A separate study (referred to herein as a mock test as well as "preliminary 'mock' test" and mock trial, further description of which are discussed later herein, including those in relation to FIG. 20) has been conducted on 30 patients in an ophthalmological setting. The patients were referred to the study based on a diagnosis of glaucoma. For each patient, a test was first assessed with a mock test stimulus to assess subject's ability to follow instructions and to gauge subject's input accuracy. Of the 30 patients, the study excluded data from three patients because of insufficient evaluation from the mock test. The remaining 27 patients were observed to be able to provide input to the system based on the observed breaks that they saw on the test stimulus. Additional candidates have been further assessed in a laboratory setting as part of the mock test beyond the 30 patients. Similar results were observed.

The mock test involves generating a simulated visual-field loss stimulation within a presented pattern and evaluating similarity and/or dissimilarities between the resulting input and the simulated stimulation. In some embodiments, the mock test is configured to simulate, i.e., present potential percepts to be experienced during the visual-field testing, including one or more absolute visual-field defects (e.g., as a stable perception of break in texture pattern), one or more relative visual-field defect (e.g., less stable break with blue color gradient over texture pattern), and no visual-field defect (i.e., no breaks, full-field texture pattern).

The mock test was used to also familiarize a subject to the test procedure as well as to assess a subject's cognitive ability to follow instructions (e.g., to fixate at the center and detect breaks in pattern elsewhere on the screen) in addition to assessing the accuracy of subject's drawing (e.g., of the outlines of the breaks).

Following a mock trial, during the visual-field test, corresponding to the first proof-of-concept test involving the exemplified systems and methods, a subject's visual-field defect is first measured using the HVF instrument. The subject's visual-field defect is then measured using the exemplified systems and methods. Because Humphrey's visual field analysis only tests the visual field at every 6-degrees of spatial interval and is based on a monocular measurement, Humphrey's visual field-based data are superimposed at every 6-degree spatial intervals over the continuously tested field results of the exemplified systems and methods.

Figure 10:
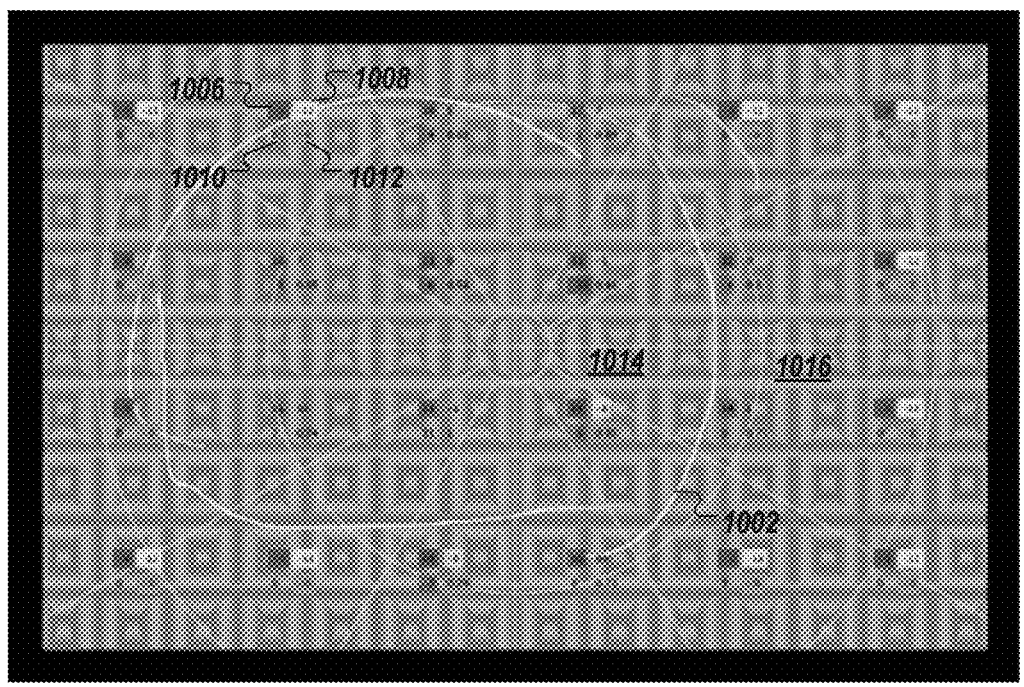
FIG. 10 and FIG. 11 each shows results of an assessment conducted via an embodiment of the exemplified systems and methods, in accordance with an illustrative embodiment.
Figure 11:
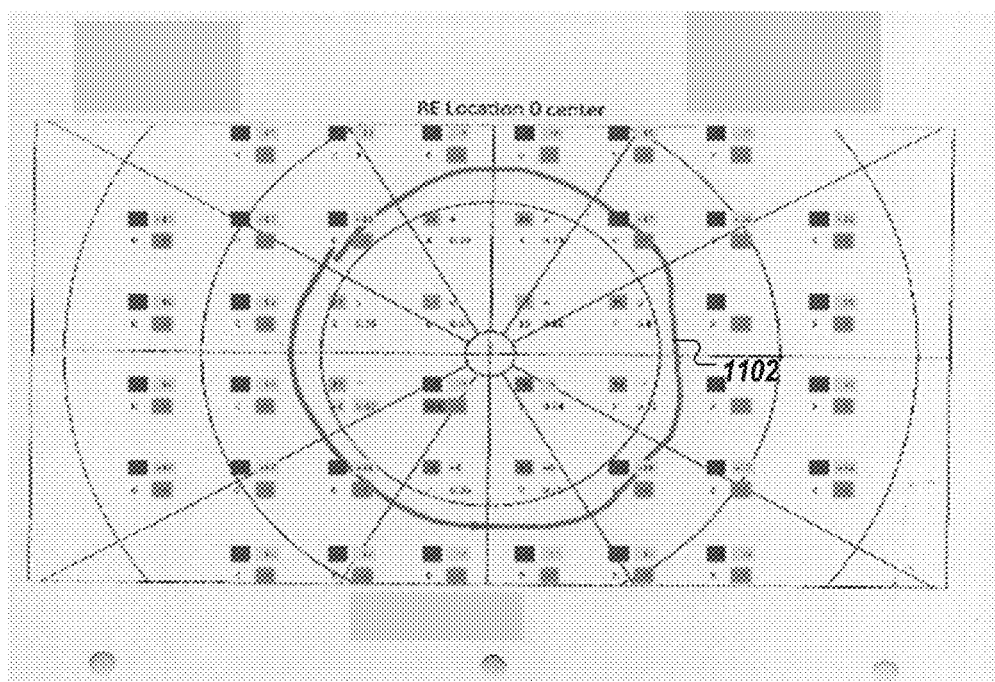

FIG. 10 and FIG. 11 each shows results of an assessment conducted via an embodiment of the exemplified systems and methods, corresponding to the exemplary visual-field test, in accordance with an illustrative embodiment. In FIGS. 10 and 11, each of the input is received on an electronic display, of a hand-held electronic device, that displays the image 102. In FIG. 10, the input is received concurrent with presentation of image 102. In FIG. 11, the input is received, from the subject, on a piece of paper, immediately after the presentation of image 102 (i.e., from memory of the subject once presentation of the image 102 has ceased).

Further shown in FIG. 10 and FIG. 11 are color boxes (1006, 1008, 1010, and 1012) with numerical values that correspond to a modeling of data derived from a corresponding Humphrey Visual Field analysis. The four models (displayed at each of the spatial intervals) correspond to a sensitivity value at each location tested (arrow 1006), a pattern deviation value at each location tested (arrow 1008), a difference in sensitivity value between the two eyes at a same tested location (arrow 1010), and a ratio value of each eye's sensitivity to the binocular summated sensitivity (arrow 1012).

The data associated with the four models are added as part of the proof-of-concept analysis and is not required for the analysis. In some embodiments, the addition of these models are added as being adjunctive and can be used for data interpretation.

As shown in FIG. 10 and FIG. 11, the inputs 1002, 1102 correspond to boundary of a break, and the break demarcates peripheral area of greater defects that generally matches the data shown via the four models 1006-1012 acquired via the Humphrey's visual field analysis. As previously noted, a visual field defect is present if the patient sees one or more breaks in the texture pattern. In FIG. 10, the subject see texture pattern inside the drawn circle (see region 1014) and see only a blue region outside the drawn circle (see region 1016). This indicates a visual field loss and/or defect.

FIG. 12 shows a table of results for four patients assessed using the exemplified methods and systems of FIGS. 10 and 11, in accordance with an illustrative embodiment.

FIGS. 13A and 13B and FIGS. 14A and 14B show two sets of respective results of an assessment of the left eye and of the right eye for a patient (i.e., the data set associated with subject "2008" shown in FIG. 12), corresponding to the exemplary visual-field test, in accordance with an illustrative embodiment.

Figure 13A:
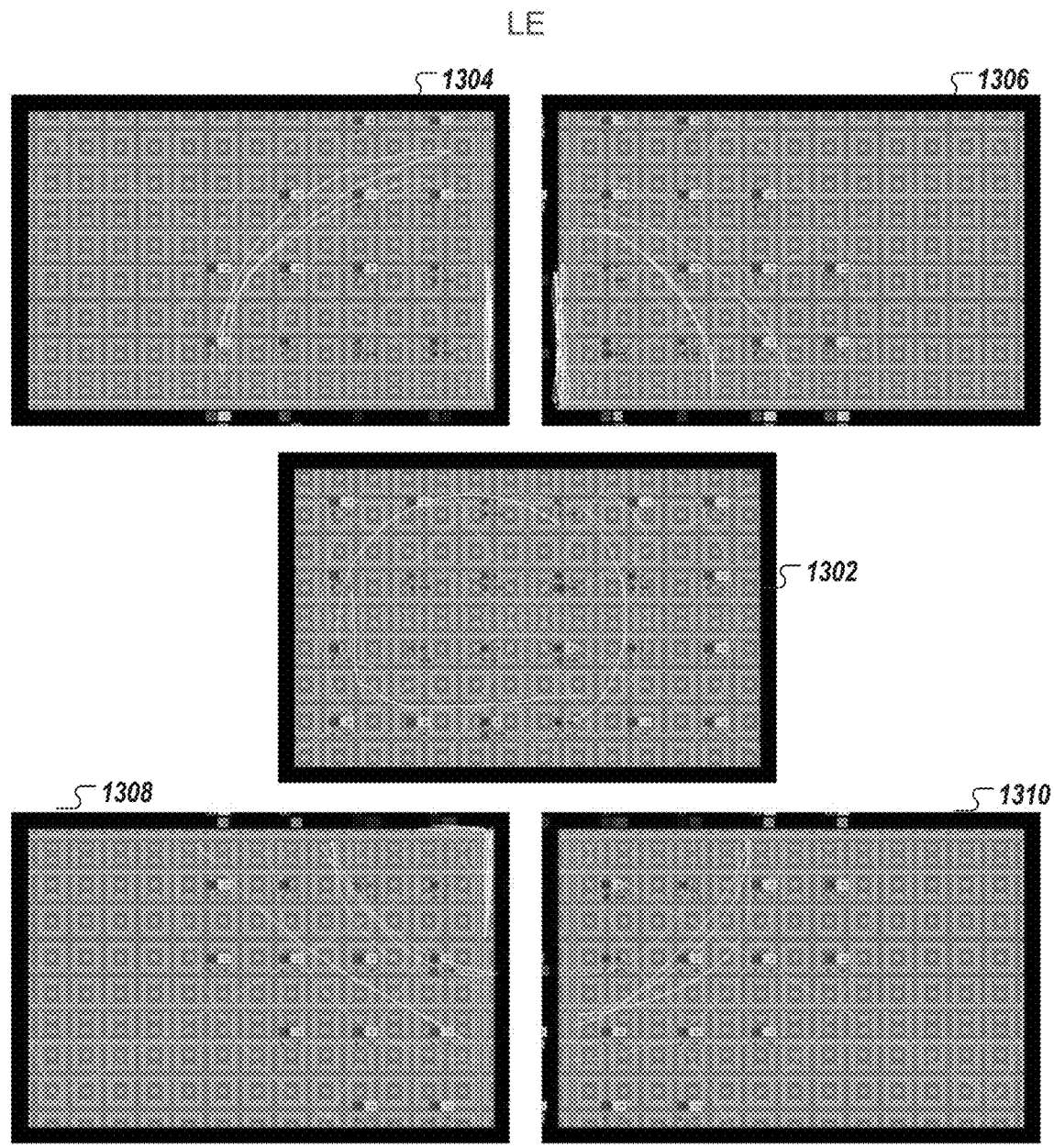
FIGS. 13A and 13B and FIGS. 14A and 14B show two sets of respective results of an assessment of the left eye and of the right eye for a patient (i.e., the data set associated with subject "2008" shown in FIG. 12), in accordance with an illustrative embodiment.
Figure 13B:
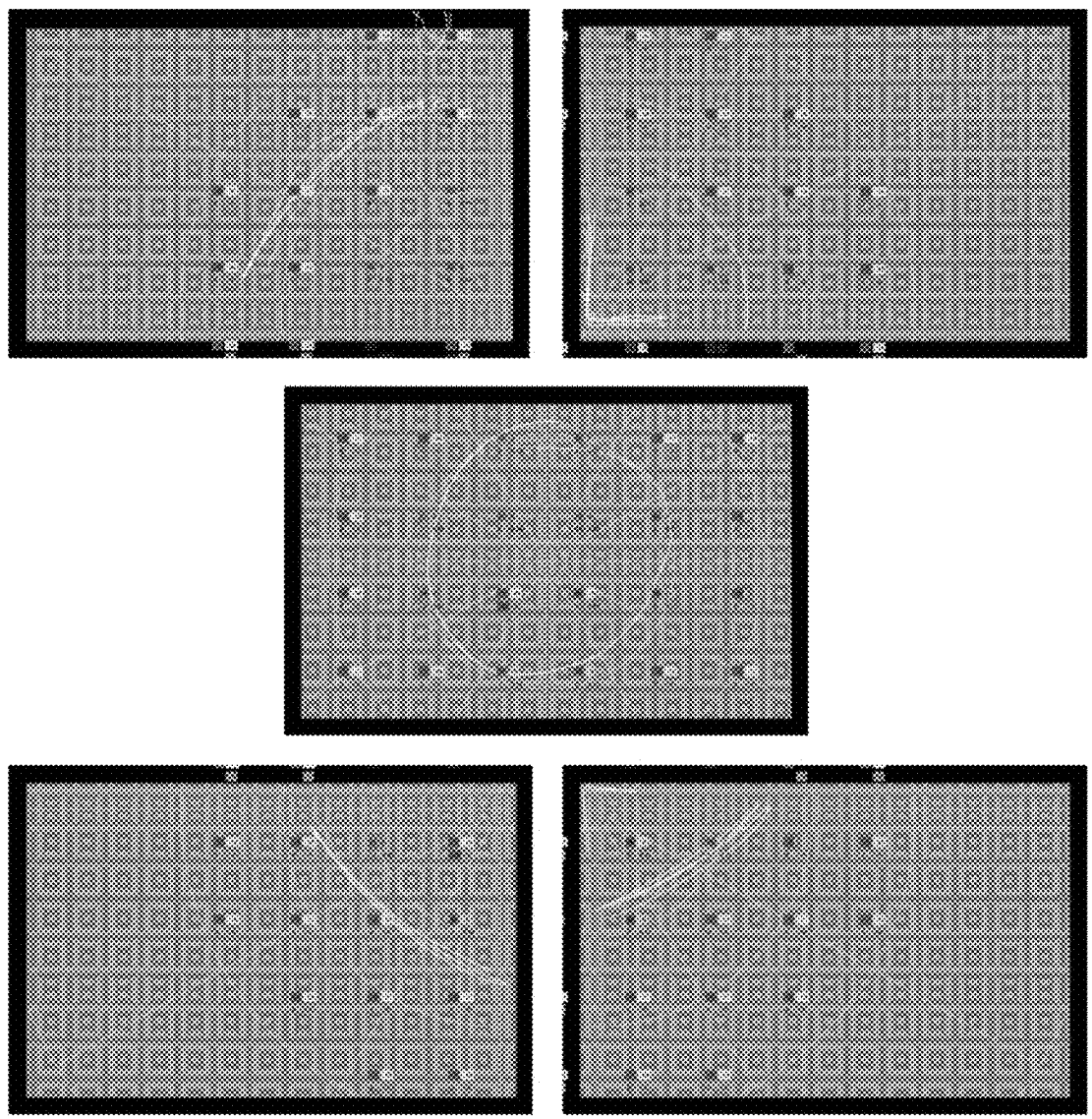
Figure 14A:
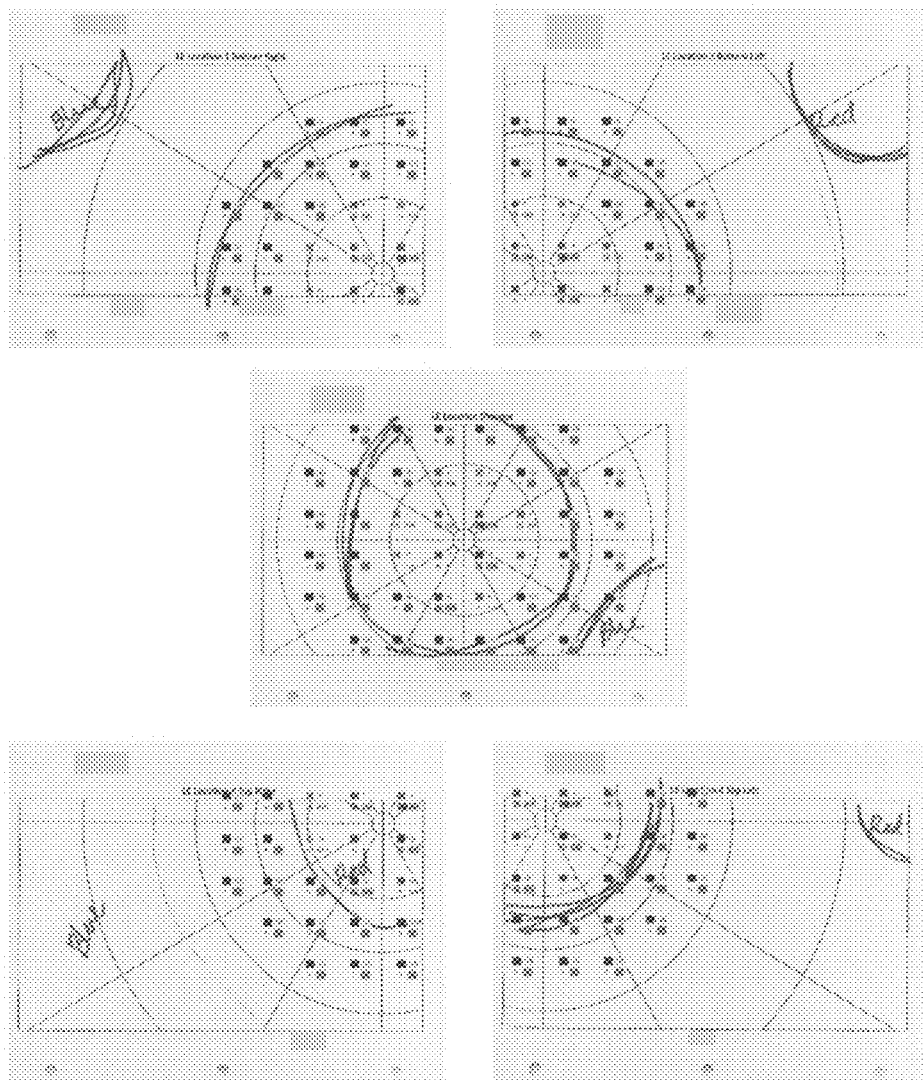
Figure 14B:
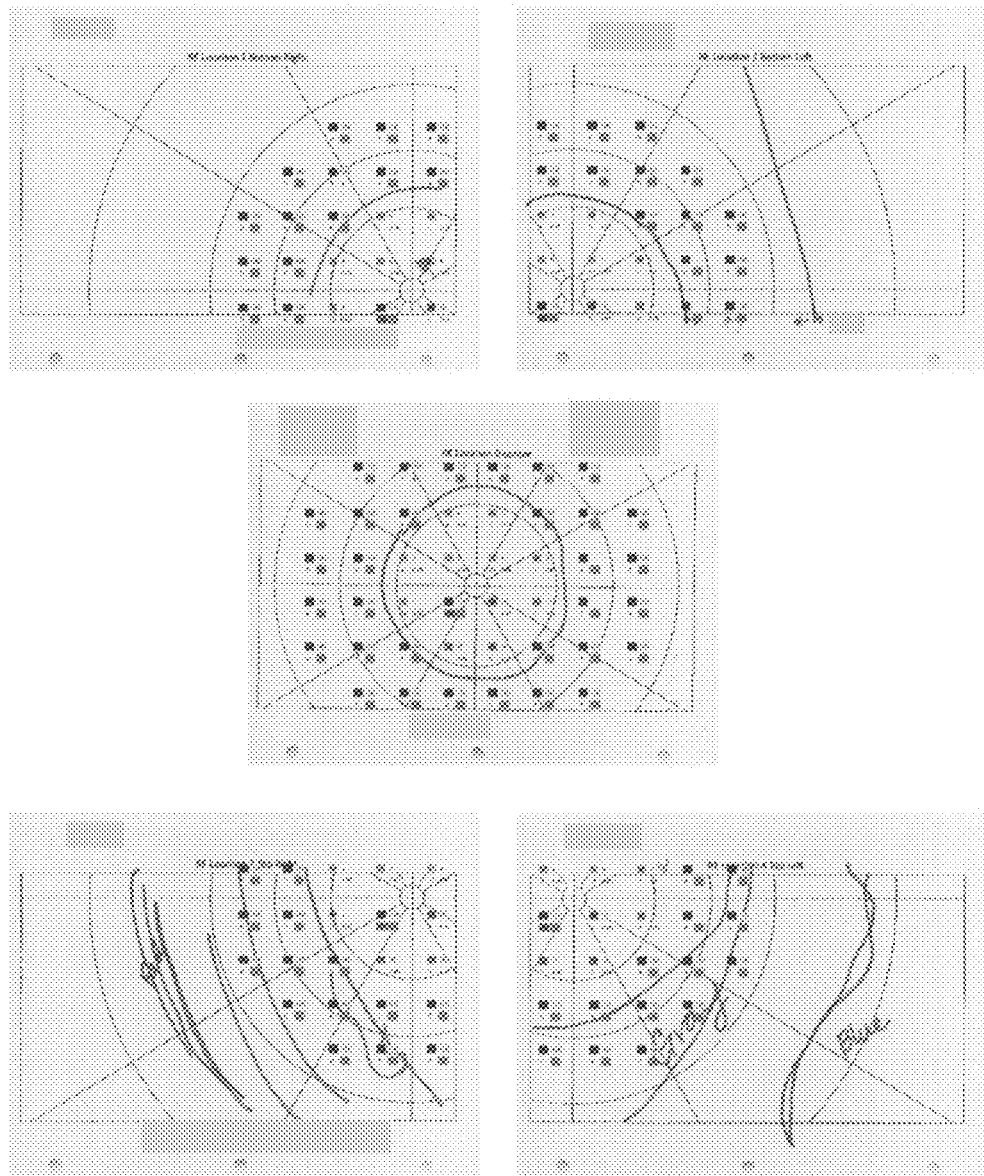
Figure 15A:
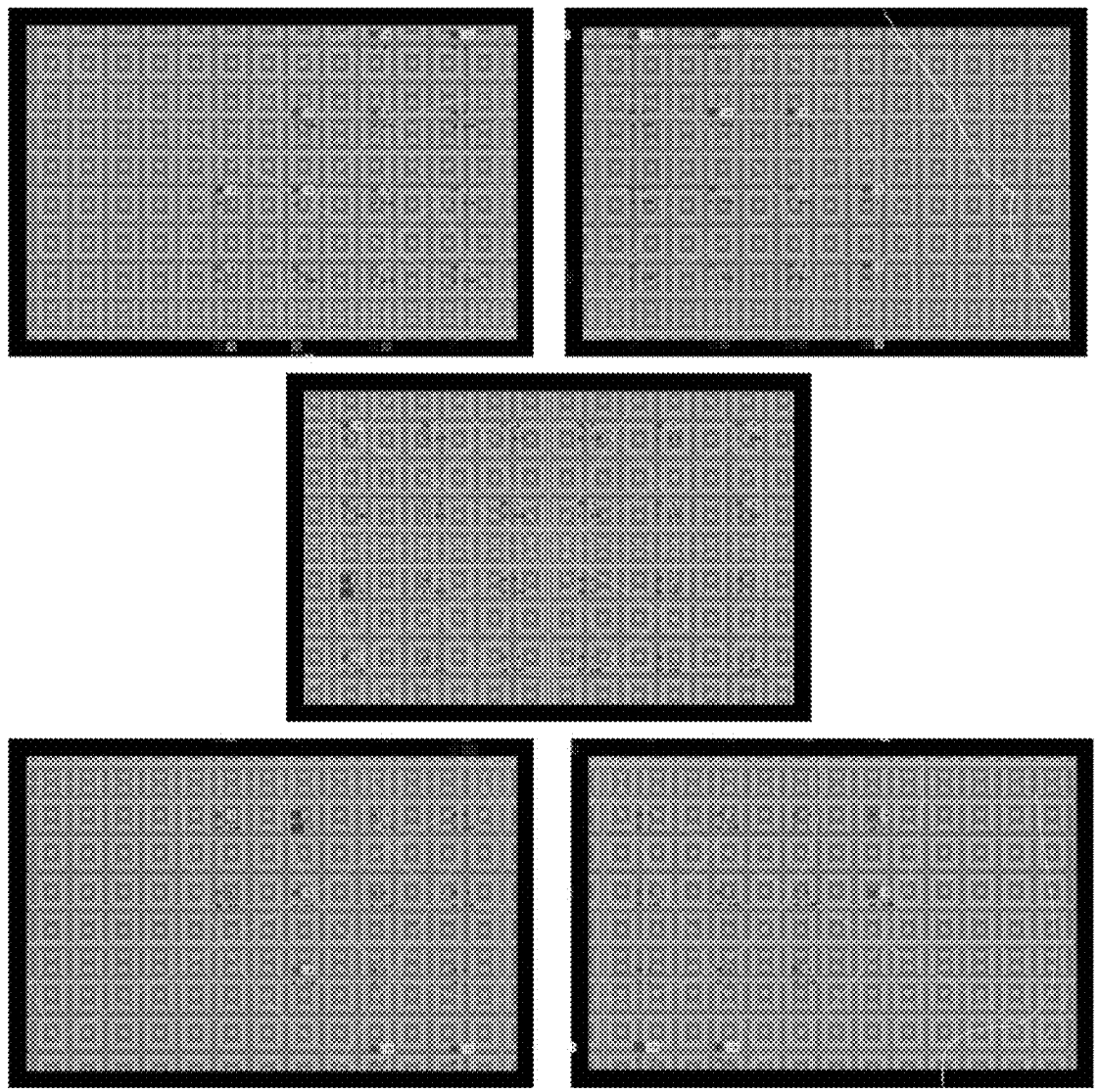
FIGS. 15A and 15B and FIGS. 16A and 16B show two sets of respective results of an assessment of the left eye and of the right eye for a patient (i.e., the data set associated with subject "2000" shown in FIG. 12), in accordance with an illustrative embodiment.
Figure 15B:
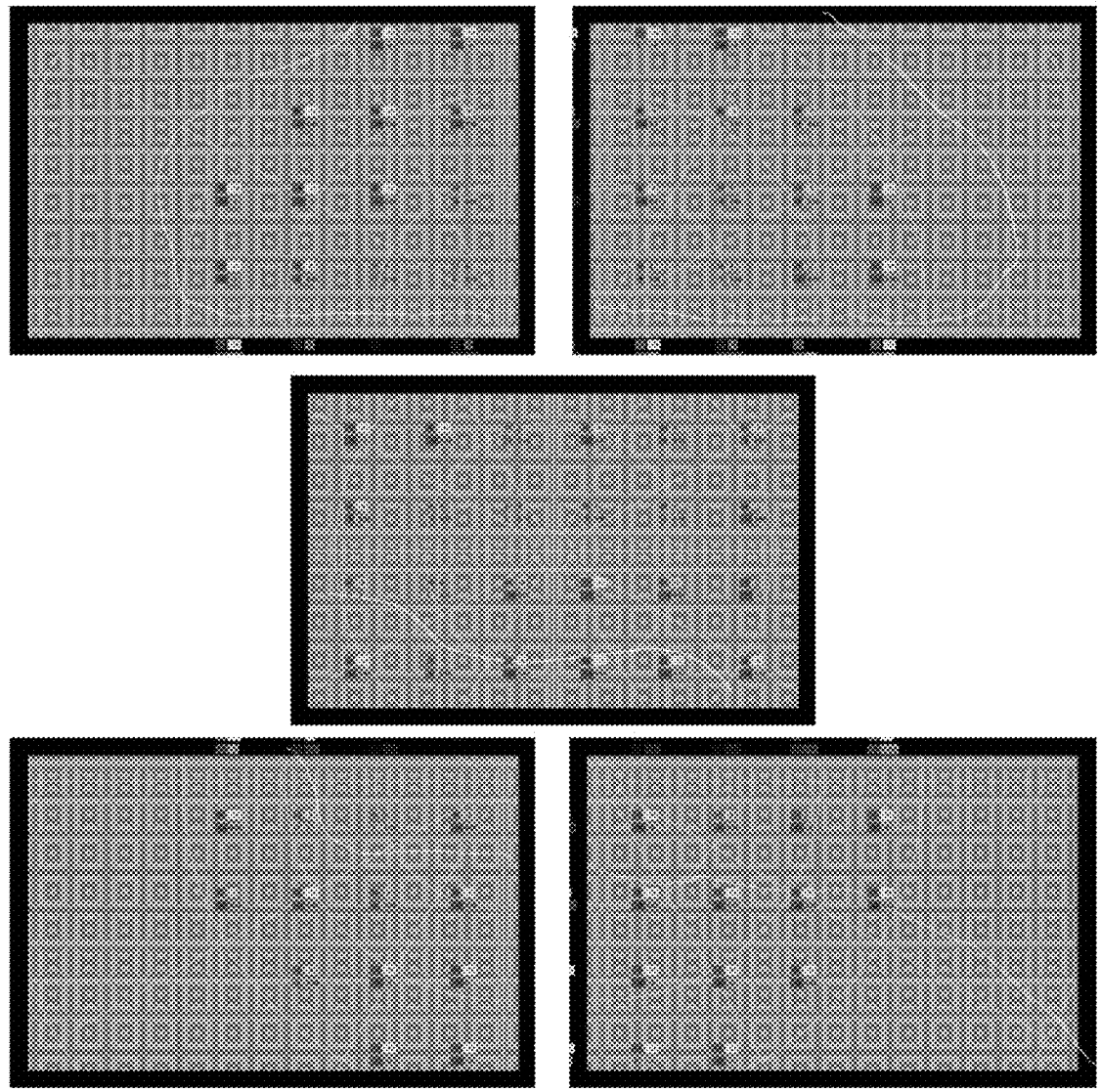
Figure 16A:
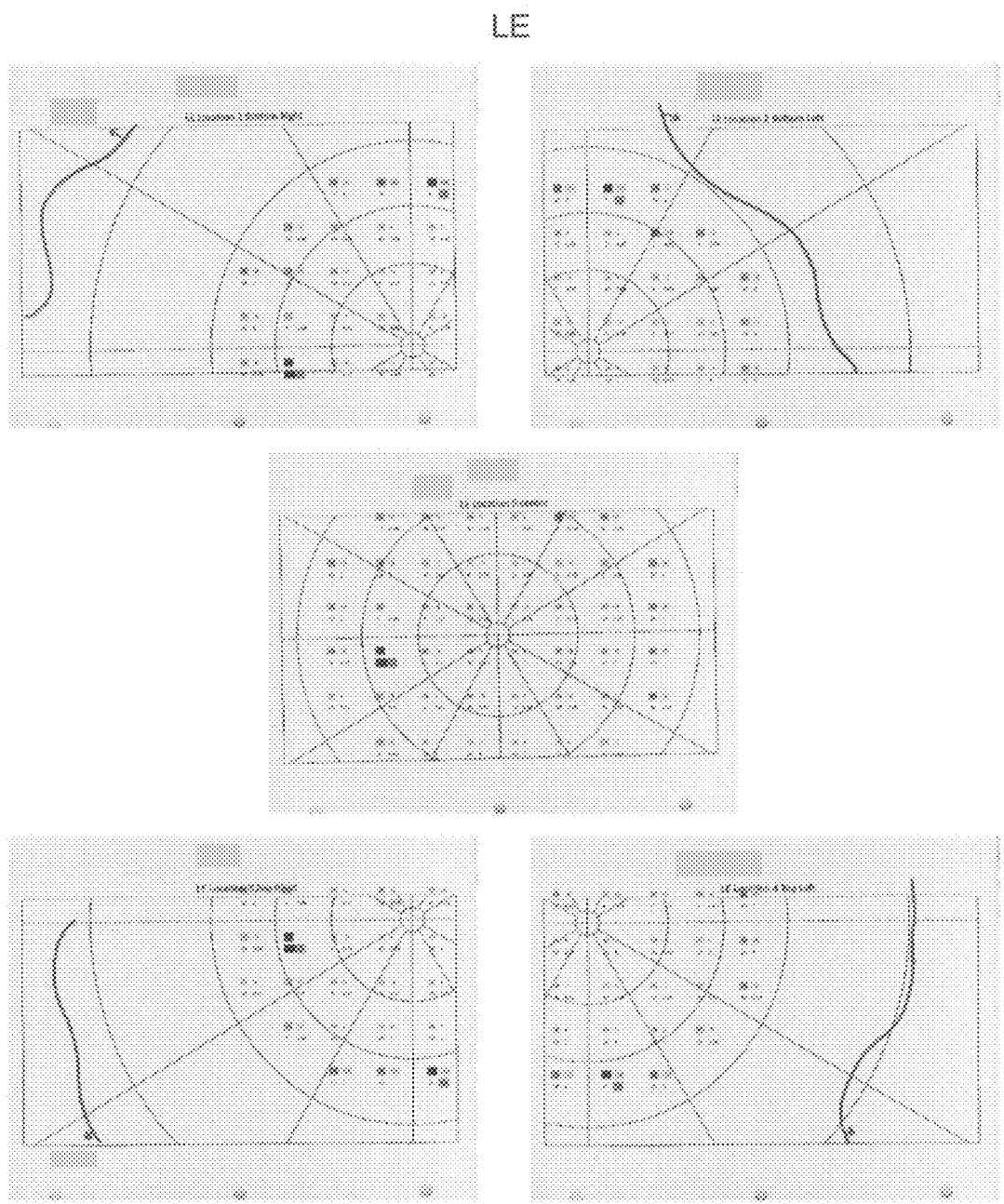
Figure 16B:
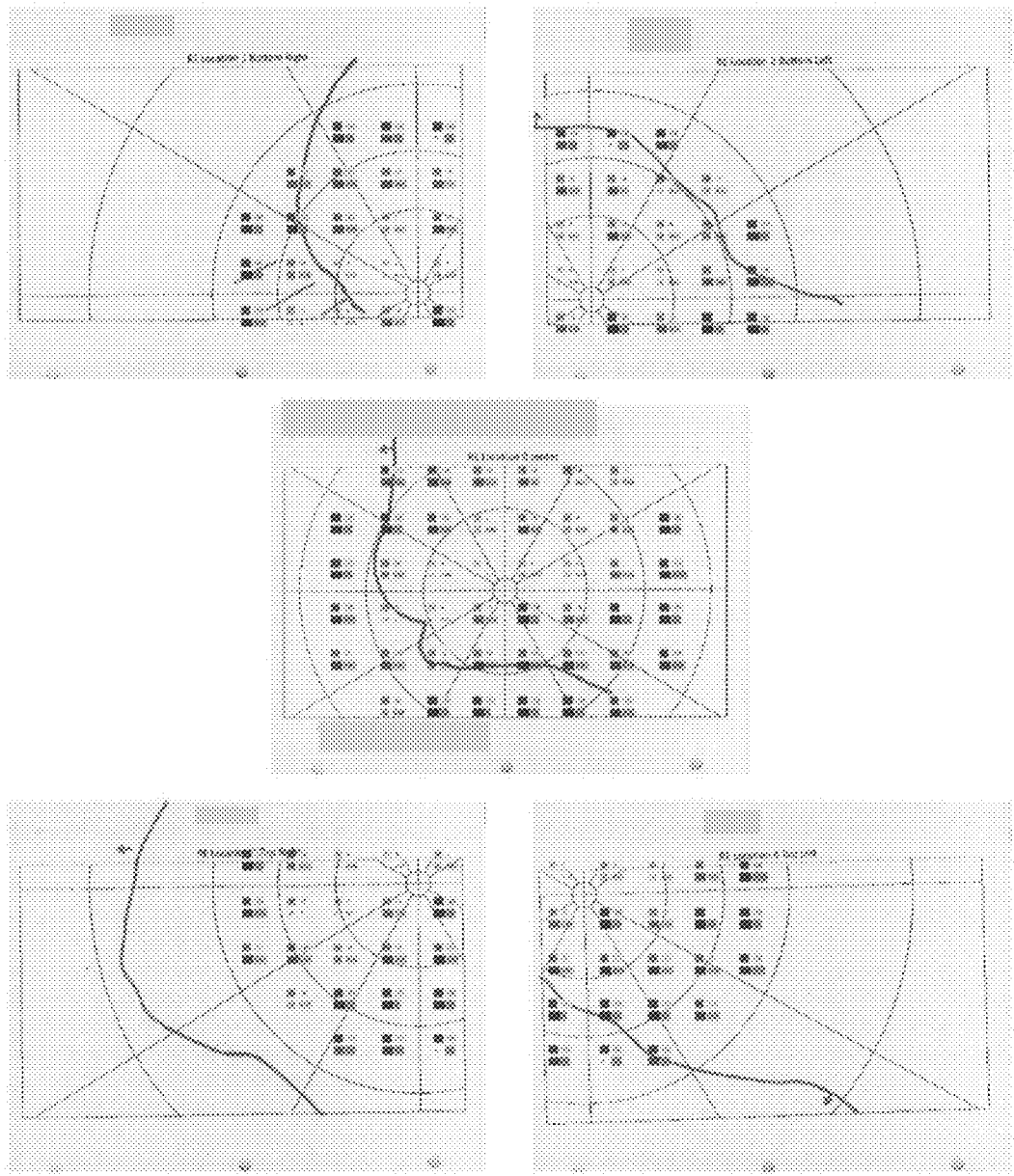
Figure 17A:
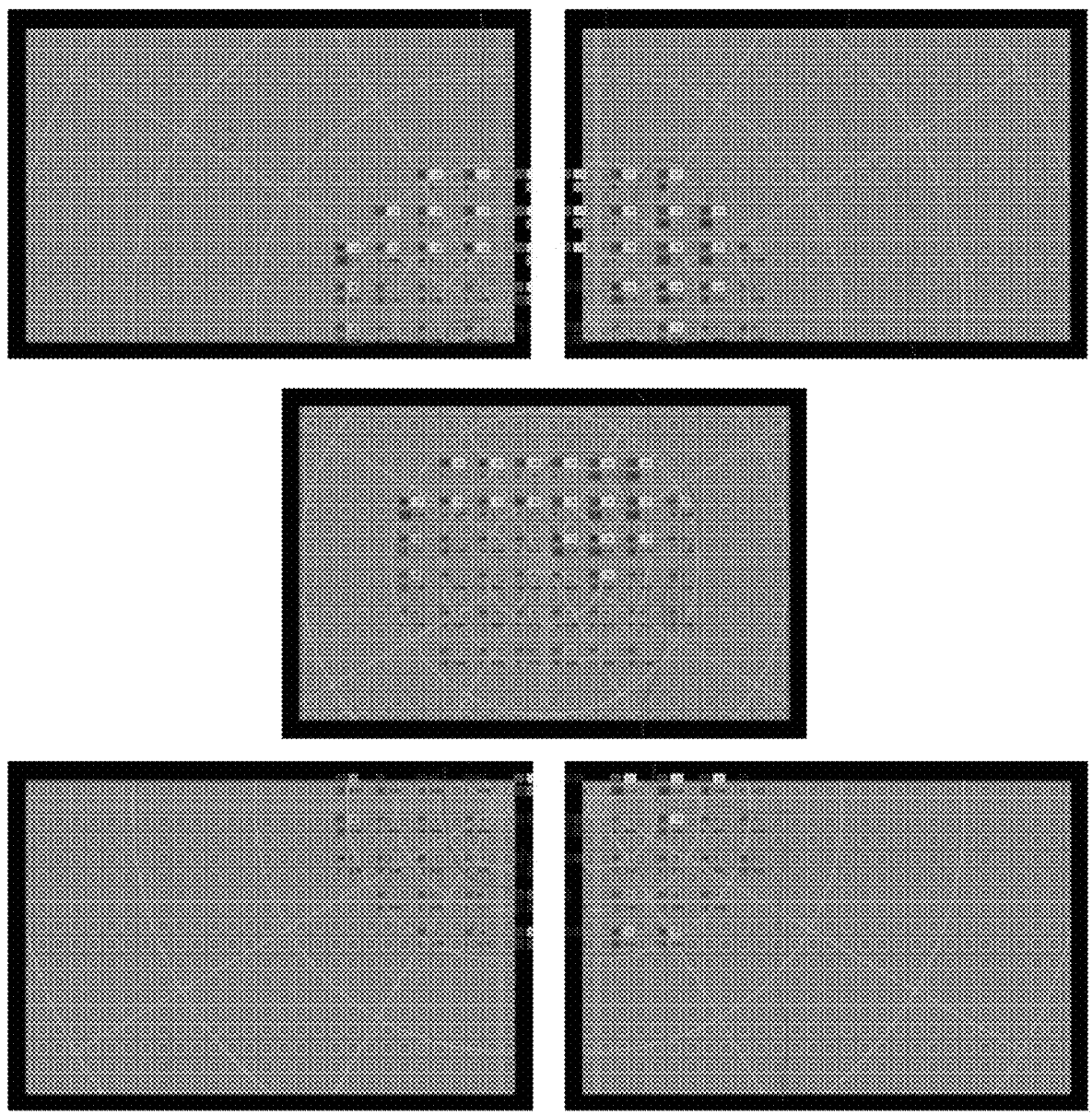
FIGS. 17A and 17B and FIGS. 18A and 18B show two sets of respective results of an assessment of the left eye and of the right eye for a patient (i.e., the data set associated with subject "2009" shown in FIG. 12), in accordance with an illustrative embodiment.
Figure 17B:
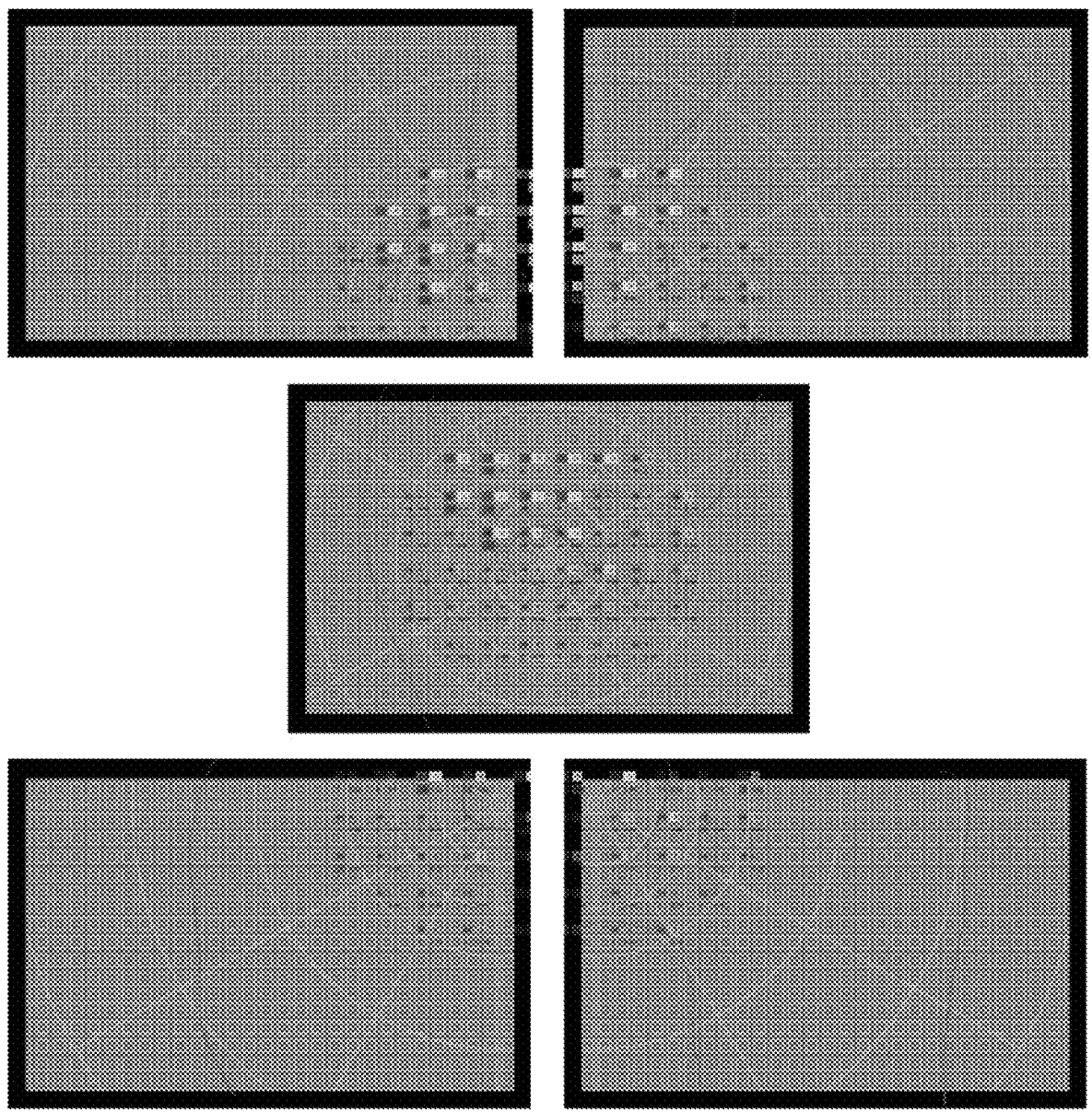
Figure 18A:
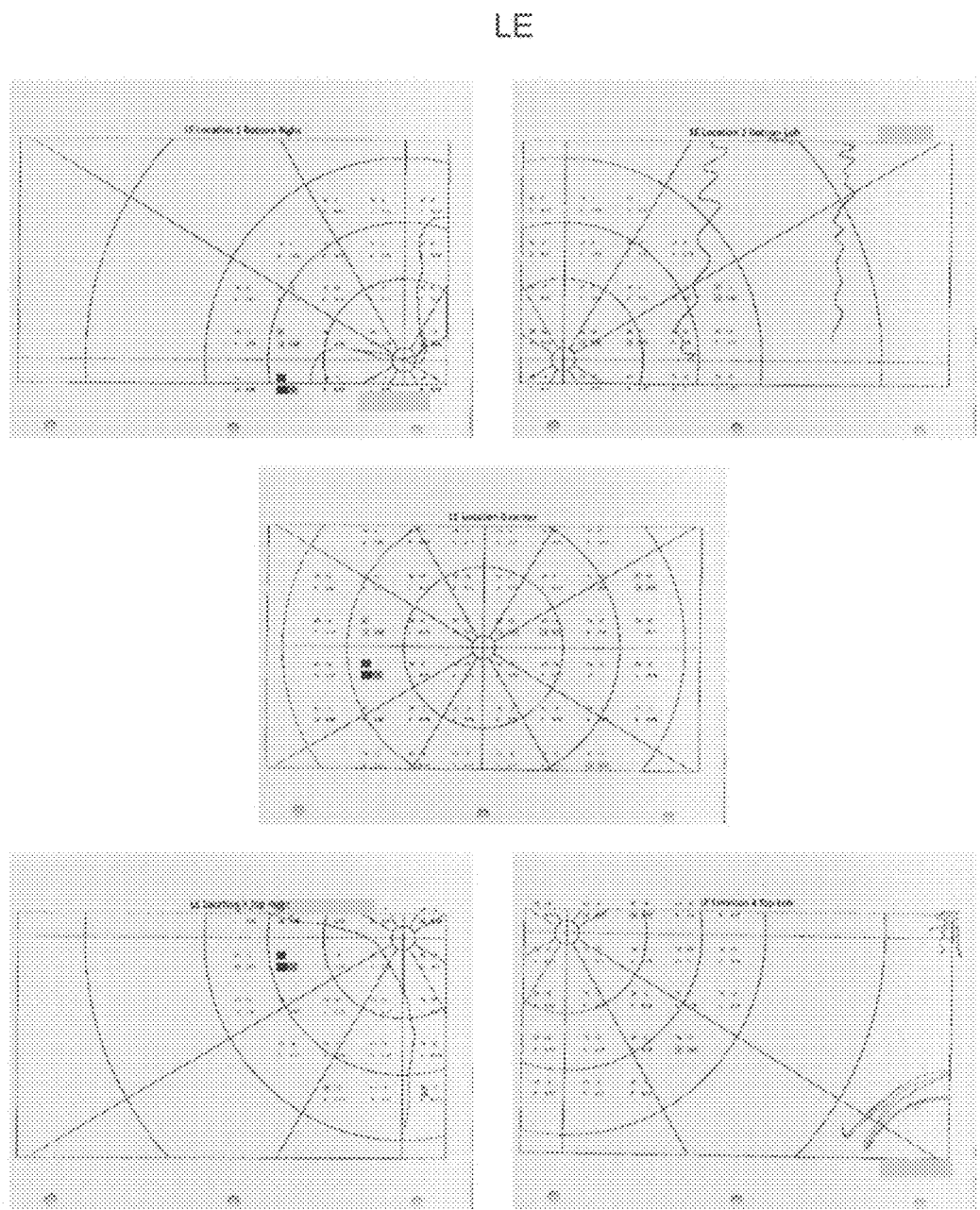
Figure 18B:
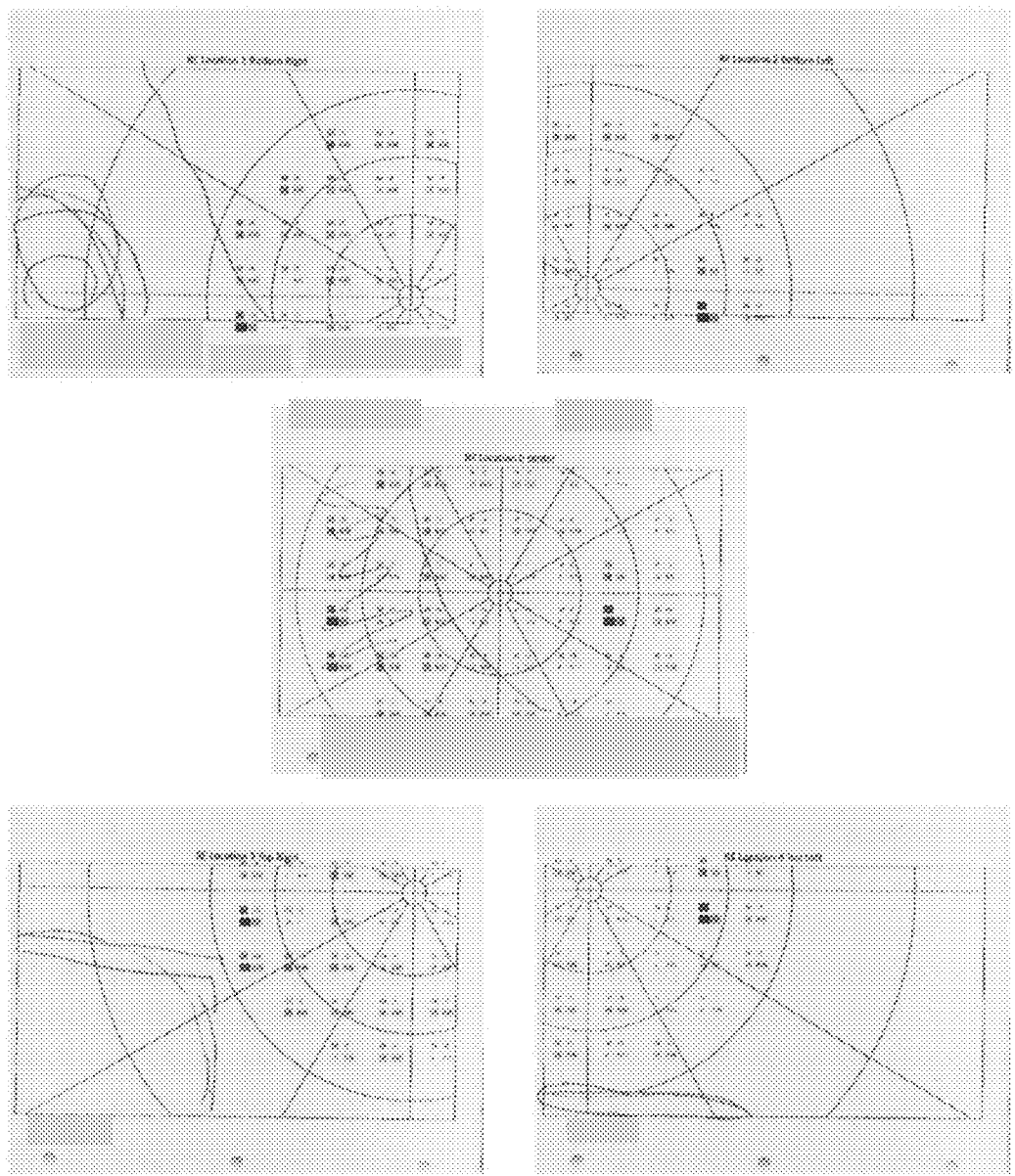

FIG. 13A shows the images 102 and captured input associated therewith for a center-target test image (1302), the first-quadrant corner target test image (1304), the second-quadrant corner target test image (1306), the third-quadrant corner target (1308), and the fourth-quadrant corner target test image (1310). The same set of test result format is shown in FIG. 13B. The test involves presenting, via a touch-screen electronic display, test images as shown in FIGS. 13A, 13B, 14A, and 14B, as static images and viewed via red-blue anaglyphic filters. In FIGS. 13A and 13B, the results are directly captured by the subject during the stimulation of the dissimilar visual scenes. In FIGS. 14A and 14B, the results are captured after the stimulation of the dissimilar visual scenes has stopped, i.e., from recollection by the subject.

FIGS. 15A and 15B and FIGS. 16A and 16B show two sets of respective results of an assessment of the left eye and of the right eye for a patient (i.e., the data set associated with subject "2000" shown in FIG. 12), corresponding to the exemplary visual-field test, in accordance with an illustrative embodiment.

FIGS. 17A and 17B and FIGS. 18A and 18B show two sets of respective results of an assessment of the left eye and of the right eye for a patient (i.e., the data set associated with subject "2009" shown in FIG. 12), corresponding to the exemplary visual-field test, in accordance with an illustrative embodiment.

Figure 27A:
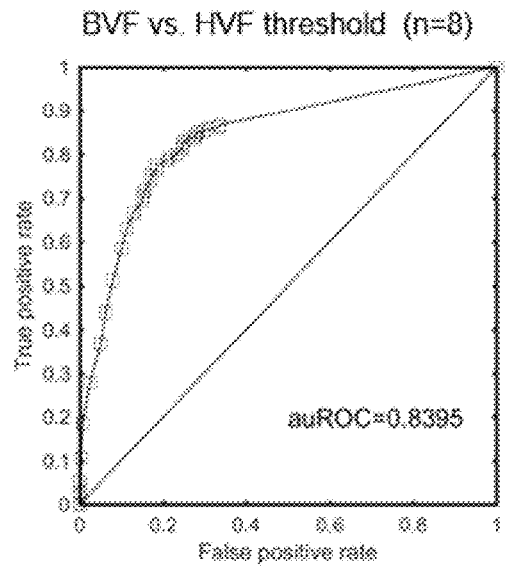
FIGS. 27A-27B show experimental results of the visual field test corresponding to those conducted in the first proof of concept study.
Figure 27B:
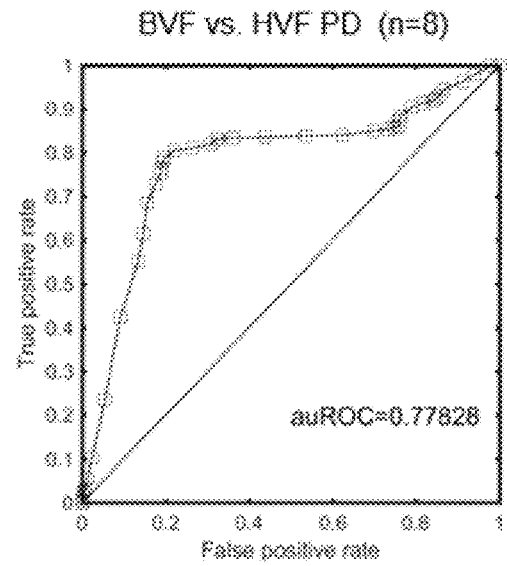

FIGS. 27A-27B show experimental results of the visual field test (also referred to as "recollection response protocol") corresponding to those conducted in the first proof of concept study. Data from subjects with visual field defects causing central and peripheral losses (due variously to retinitis pigmentosa, ocular histoplasmosis, Stargard's disease and occipital lobe stroke) were analyzed for correspondence between HVF and BVF methods. Collectively, the extent of the patients' visual field defects, as represented by HVA's Mean Deviation (MD) index was −16.2±8.5 dB.

The central 24 deg of the visual field data were analyzed because HVF were obtained with the SITA 24-2 protocol. Threshold and pattern deviation (PD) data from HVF were compared with the areas demarcated by the subjects as being seen as "texture rich pattern" (normal visual field) vs "no texture impoverish scene" (defective visual field). A receiver operating characteristic (ROC) analysis was used to compare these 2 groups of data.

In FIGS. 27A and 27B, the HVF with BVF data obtained from 8 subjects' responses drawn from recollection/memory (similar to the individual examples shown in FIGS. 14, 16, and 18) were compared. FIGS. 27A and 27B, respectively, show the ROC curves comparing the BVF data with the HVF threshold and with the PD data. The area under the curve (AuROC) for each graph reveals good correspondence between the HVF and BVF data.

Figure 21:
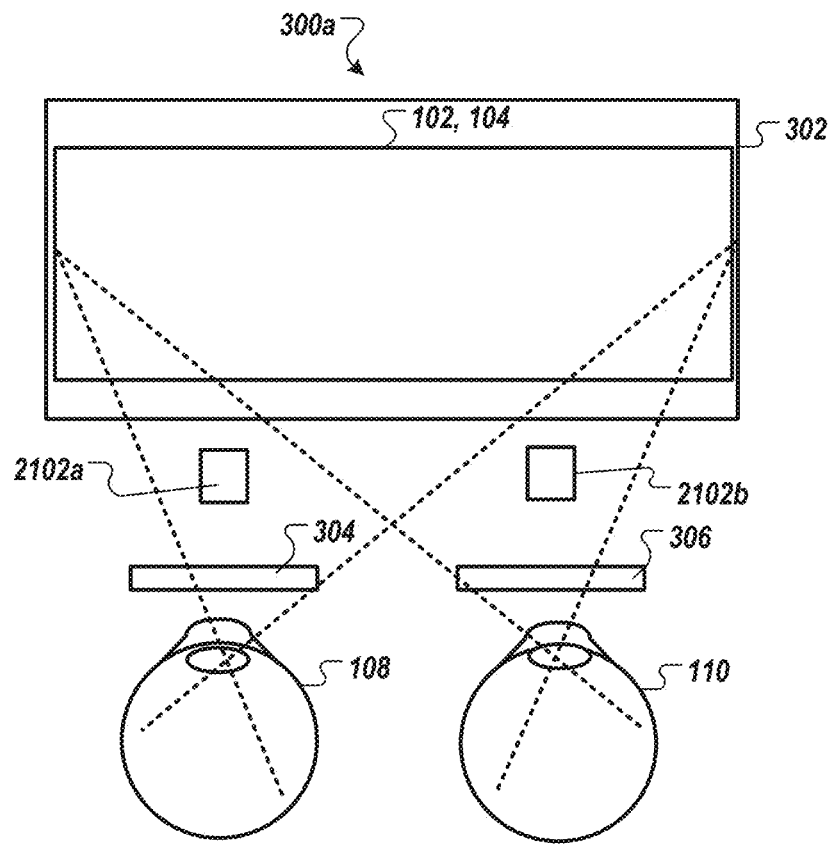
FIGS. 21 and 22 shows the system for contemporaneously and concurrently presenting dissimilar visual scenes to a person to stimulate both eyes for the assessment of visual field of the person of FIGS. 3 and 4, respectively, configured with one or more eye tracking sensors or scanners, in accordance with an illustrative embodiment.
Figure 22:
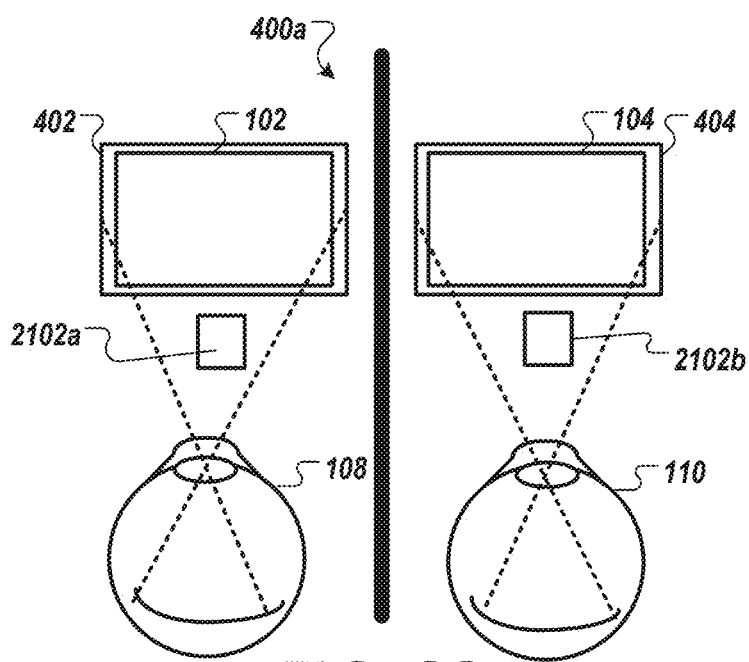
Figure 23:
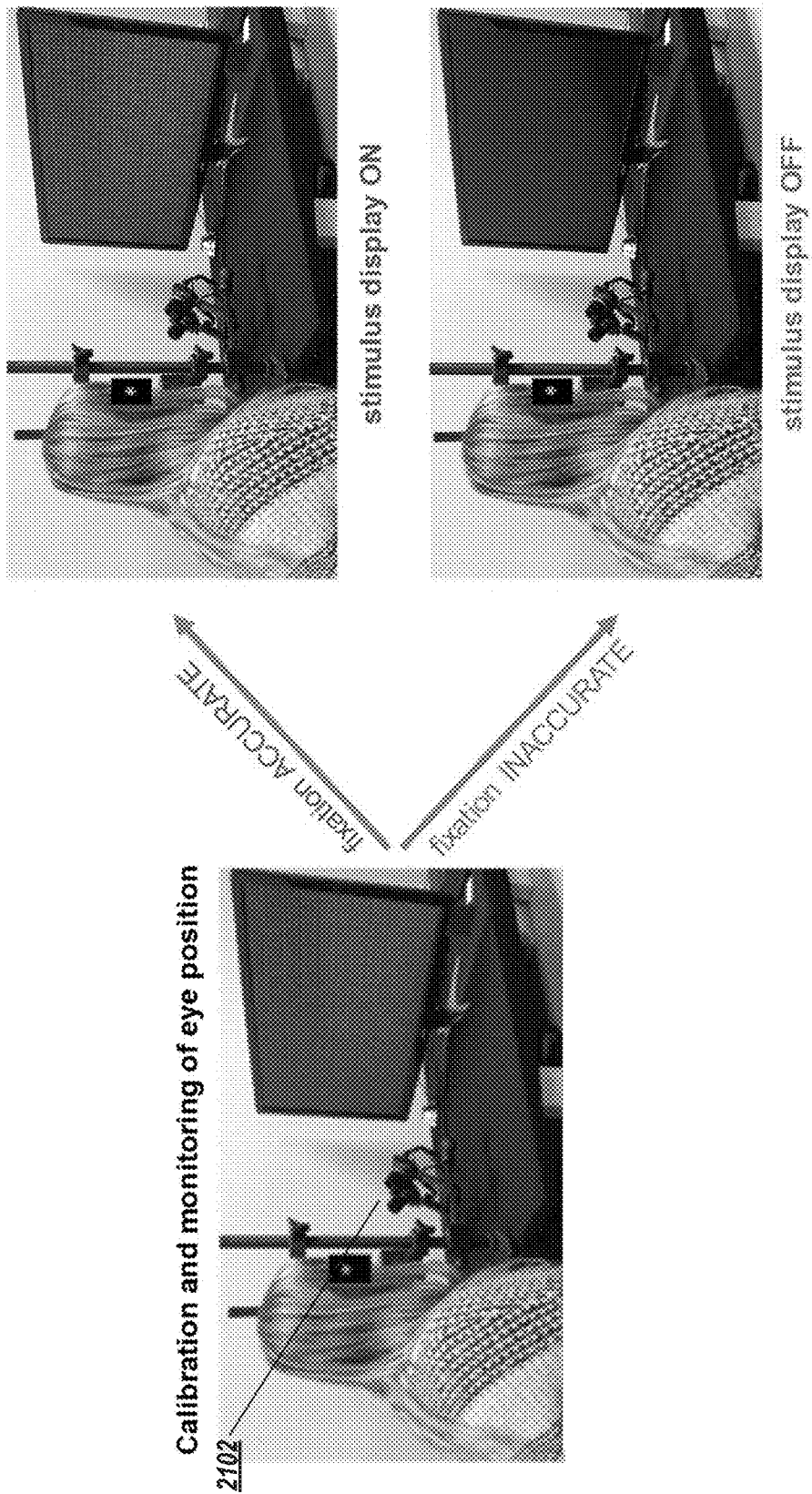
FIG. 23 shows an experimental setup of the system of FIG. 21 configured with the one or more eye tracking sensors or scanners, in accordance with an illustrative embodiment.
Figure 28A:
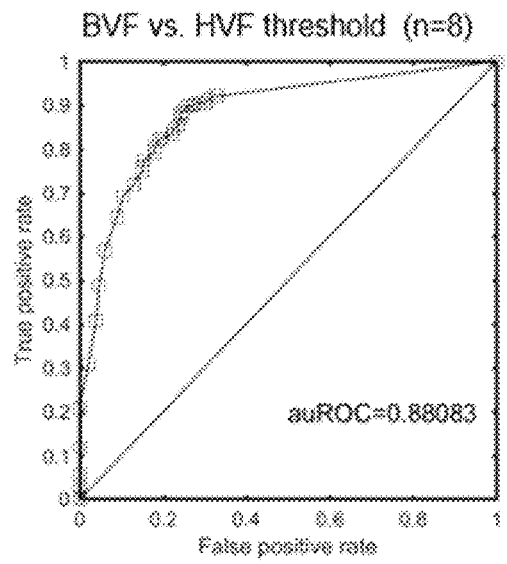
FIGS. 28A-28B show experimental results of the visual field test with eye-tracking control.
Figure 28B:
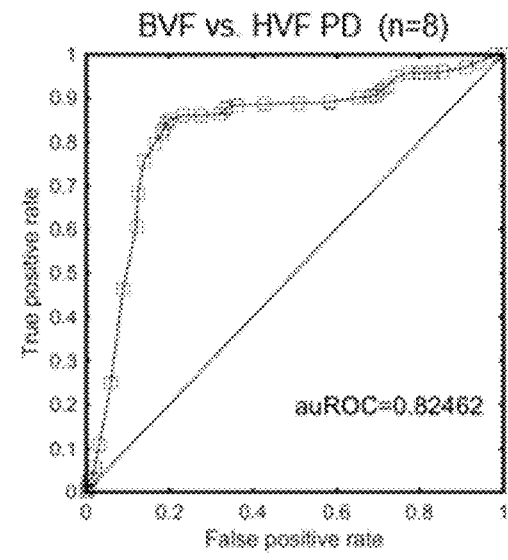

Additionally, the same subjects whose results were shown in FIGS. 27A and 27B were also tested using the eye tracking control protocol (as discussed in relation to FIGS. 21, 22, and 23). FIGS. 28A and 28B show the ROC curves comparing the BVF data, respectively, with the HVF threshold and PD data with respect to the eye tracking control protocol. The area under the curve (AuROC) for each graph reveals good correspondence between the HVF and BVF data.

A second proof-of-concept experiment (referred to herein as "second proof-of-concept experiment") was conducted to simulate HVF testing protocol in the BVF test setup by mapping the subject's visual-field in the HVF test environment. In this visual-field test, the subject is requested to indicate whether he/she saw the test stimulus when the viewing distance was fixed by restraining the subject's head with a head-and-chin rest.

Smaller sizes test stimuli (diameters: 6°, 3° and 1.5°) were used to map the visual-field loss of subjects (referred to as "BVF mapping"). This experiment shows good agreement between the HVF testing and the reduced-sized test stimuli visual-field testing. FIG. 26 shows experimental results of two BVF mappings (shown as 2602 and 2604) generated from experiments using smaller sizes test stimuli and same BVF mapping superimposed over corresponding HVF mappings (shown as 2606 and 2608, respectively), in accordance with an illustrative embodiment. The study also concluded that inputs of texture pattern can vary due to accuracy of subject in reproducing the observed patterns as drawing lines without looking directly at the input and due to minor variability in viewing distance while the subject is performing the test.

Figure 29A:
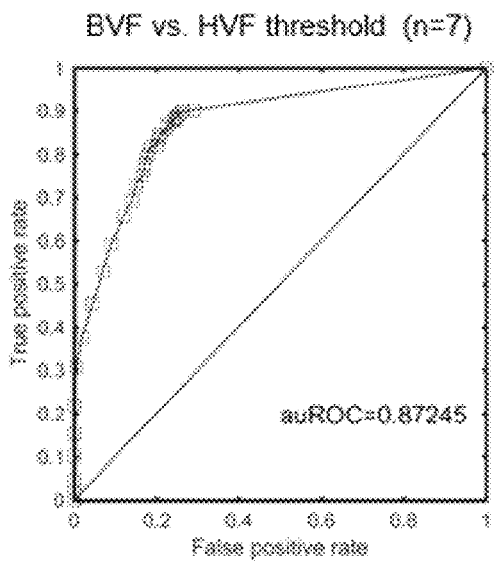
FIGS. 29A-29B show experimental results of the visual field test corresponding to those conducted in the second proof of concept study.
Figure 29B:
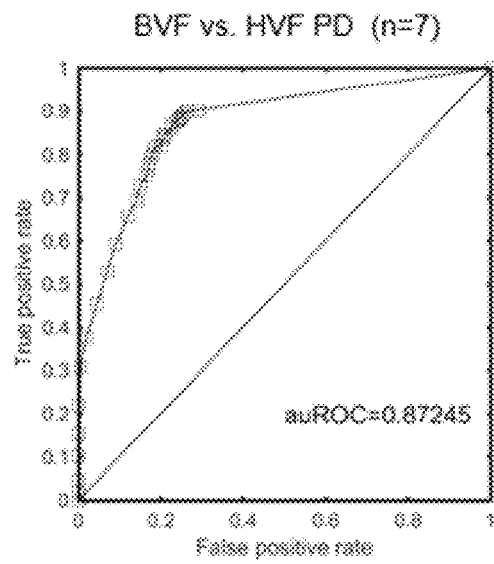

FIGS. 29A-29B show experimental results of the second proof-of-concept experiment. Seven subjects with visual field defects causing central and peripheral losses (due to glaucoma, retinitis pigmentosa, Stargard's disease, ocular histoplasmosis and occipital lobe stroke) were tested on the proof-of-concept control experiment, e.g., as discussed in relation to FIG. 26. Collectively, the extent of the patients' visual field defects, as represented by HVF's Mean Deviation (MD) index was −13.3±9.2 dB.

The BVF data obtained were compared with their HVF threshold and pattern deviation (PD) data. The central 24 deg of the visual field data were analyzed because HVF were obtained with the SITA 24-2 protocol. FIGS. 29A and 29B show the ROC analysis comparing the BVF data, respectively, with the HVF threshold and PD data. The area under the curve (AuROC) for each graph reveals good correspondence between the HVF and BVF data.

Example Method of Operation of the Visual Field Test

Figure 19:
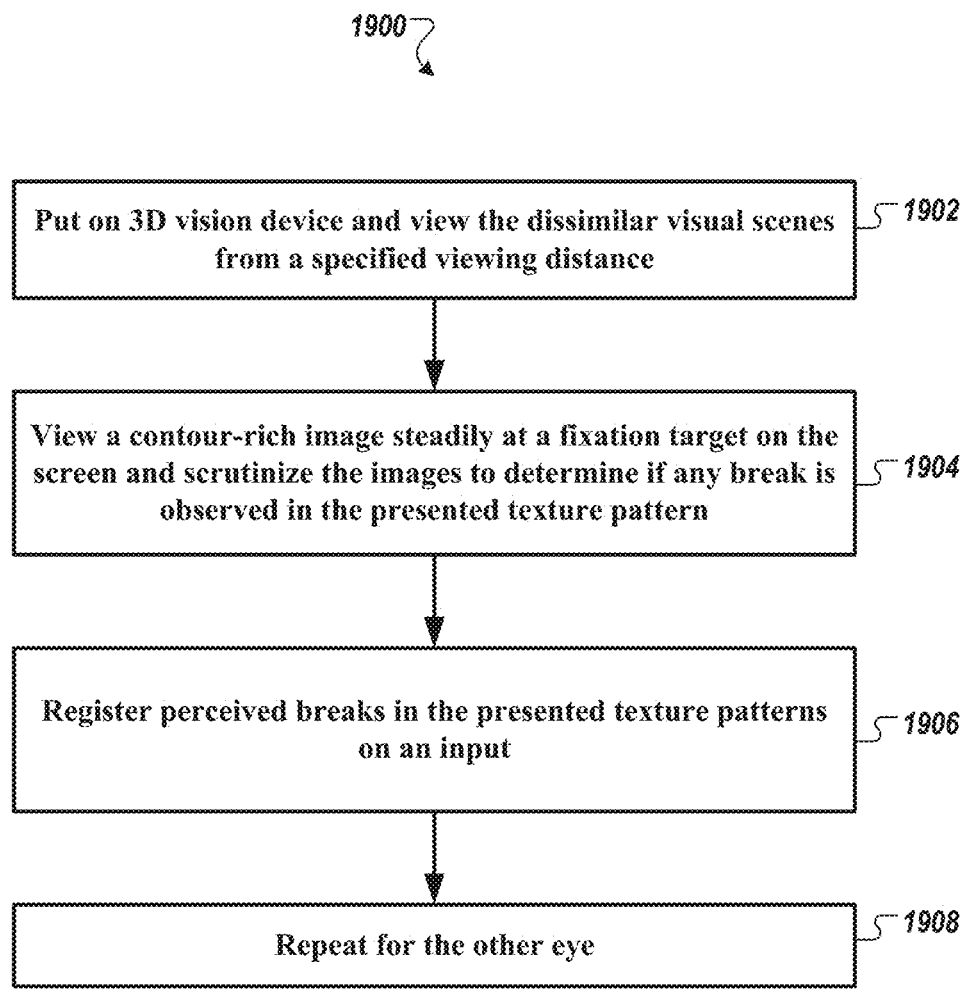
FIG. 19 is a flowchart of an example process of assessing and/or measuring a person's visual field, in accordance with an illustrative embodiment.

FIG. 19 is a flowchart of an example process 1900 of assessing and/or measuring a person's visual field, in accordance with an illustrative embodiment.

The subject is first instructed (1902) to put on a 3D-vision-device. The subject is also instructed to view the images on the electronic screen or on paper from a specific viewing distance. The viewing distance can depend on the desired visual field extent (angle) to be tested.

The subject is also instructed (1904) to look steadily at a fixation target on the screen or paper. The fixation target could be first located at the center of the image. For a smaller screen size (e.g., for display or paper), the fixation target could be located successively at each of the four corners of the screen (paper). The subject is also instructed to, while looking at the fixation target, use side vision to scrutinize the entire image to see if any break is seen in the textured pattern. The break could be observed as a colored patch with or without the textured patterns. The break should be readily noticeable within a few seconds of steady fixation. (The area of the break indicates the visual field is defective in that region.).

The subject is then instructed (1906) to register their perception of each break that is observed by the subject by either drawing it on the device's touch screen or verbally describing it and drawing on a piece of paper. If no break is seen, then no visual field defect is assessed to be detected in the tested eye. When, both blue (non-tested eye image) and texture pattern (tested eye image) are seen at a same region, then a possible defect is assessed because both eyes are seeing their respective images rather than the tested-eye alone. When, blue texture-free area/zone (non-tested fellow eye image) is seen in the far periphery instead of the red texture pattern, then no defect is assessed—blue is seen on the left periphery when right eye is tested, or seen in the right periphery when left eye is tested. This is normal as the far temporal field of each eye is more sensitivity in normal visual system.

The subject is then instructed (1908) to repeat the same testing procedure for the fellow eye to be tested. In some embodiment, the dissimilar visual scenes are switched between the output portion of the electronic display. In other embodiments, a different printed material with a different dissimilar visual scenes is presented.

Preliminary "Mock" Test for Visual-Field Assessment/Measurement

In another aspect, the system is configured to generate and present one or more simulated visual-field loss stimulation within a set of dissimilar views as part of a preliminary "mock" test prior to the actual visual-field assessment/measurement test.

Figure 20:
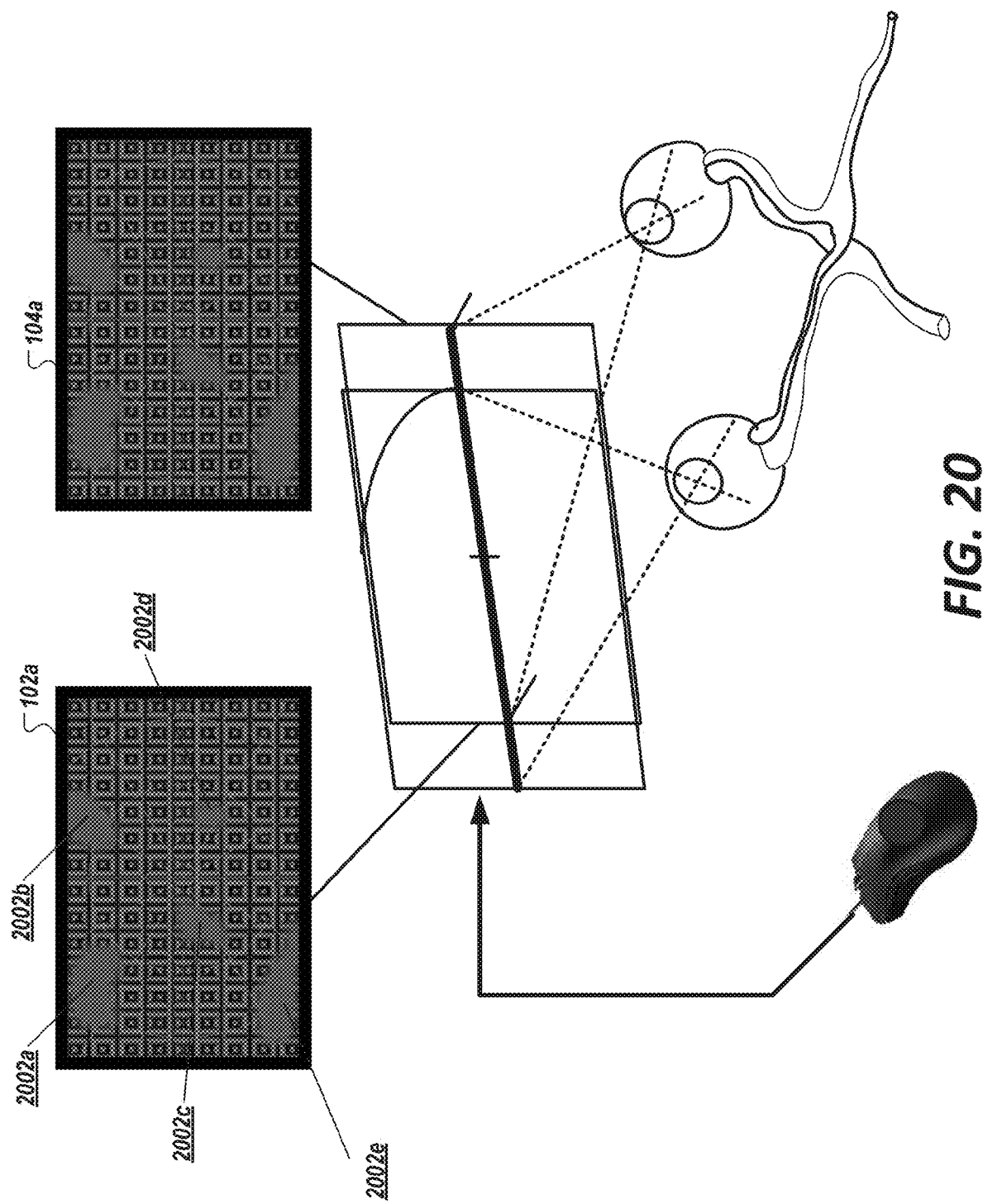
FIG. 20 shows an example set of dissimilar visual scenes that includes simulated visual-field loss, in accordance with an illustrative embodiment.

FIG. 20 shows an example set of dissimilar visual scenes that includes simulated visual-field loss 2002 (shown as 2002a, 2002b, 2002c, 2002d, and 2002e), in accordance with an illustrative embodiment. The system is configured to present the same visual scenes 102a which include the simulated visual-field loss to both eyes.

The system, in some embodiments, is configured to present the simulated visual-field loss as one or more colored patch, in some embodiments, or as a break in the textured pattern.

The mock test is configured to simulate the condition of the visual-field test by presenting potential percepts to be experienced during the visual-field testing, including one or more absolute visual-field defects (e.g., to evaluate stable and/or unstable perception of break in texture pattern), one or more relative visual-field defect (e.g., less stable break with blue color gradient over texture pattern), and no visual-field defect (i.e., no breaks, full-field texture pattern).

The mock test may be used to familiarize a subject to the test procedure as well as to assess a subject's cognitive ability to follow instructions (e.g., to fixate at the center and detect breaks in pattern elsewhere on the screen) in addition to assessing the accuracy of subject's drawing (e.g., of the outlines of the breaks). In some embodiments, the mock test includes an assessment of the subject's ability to maintain accurate eye fixation (e.g., via use of an eye tracking system). In some embodiments, the mock test includes generating, e.g., by the system, an accuracy index or score by evaluating similarity and/or dissimilarities between the resulting input and the simulated stimulation. The preliminary "mock" test is performed using the same input as the visual-field assessment/measurement.

Eye Tracking System for Visual-Field Assessment/Measurement

FIGS. 21 and 22 shows the system for contemporaneously and concurrently presenting dissimilar visual scenes to a person to stimulate both eyes for the assessment of visual field of the person of FIGS. 3 and 4, respectively, configured with one or more eye tracking sensors or scanners 2102 (shown as 2102a and 2102b), in accordance with an illustrative embodiment.

In FIG. 21, the system 300a includes a single visual source 302 (e.g., an electronic display or a printed material), and the two eyes (108, 110) are allowed to view different image scenes (e.g., 102, 104) by use of optical filters 304, 306 that allows only respective images (e.g., 102, 104) of the different image scenes to be observed by each of the eye (108, 110) (i.e., when both eyes are open). In some embodiments, the optical filters 304, 306 include color filter glass elements (e.g., to form an anaglyph or stereoscopic device). In other embodiments, the optical filters 304, 306 include polarizing filter glass elements. Other types of optical filters can be used so as to allow separate visual scenes to be presented to the two eyes (108, 110) such as a phase-haploscopic goggles (e.g., phase-haploscopic LC goggles). The visual source 302 is configured to output each scenes of the dissimilar visual scenes according to the configuration of the optical filters 304, 306. The visual source 302 may be a projector display, a desktop display, a laptop display, a tablet display, and a display mobile device that can be adapted to span a substantial portion of a person's visual field with sufficient contrast or display resolution. In FIG. 22, the system 400a includes two independent display outputs 402, 404 to provide the dissimilar visual scenes to each of the two eyes (108, 110). The two independent display outputs 402, 404 may be part of a haploscopic device, a stereoscopic device, a 3D virtual-reality head gear, or an augmented reality glass wear.

The eye tracking sensor or scanner 2102 is configured to record one or more eye positions of a subject while a subject is performing a visual-field assessment/measurement test. The recorded eye position can be correlated or compared to a set of pre-defined positions during the portion of the test when the eye is expected to fixate on a given presented target.

In some embodiments, the eye tracking sensor or scanner 2102 includes two or more sensor in which at least one sensor is used to monitor each eye. In other embodiments, the eye tracking sensor or scanner 2102 includes a single sensor (e.g., CCD camera) to capture a video feed of eyes from which individual eye positions can be assessed. In yet other embodiments, the eye tracking sensor or scanner 2102 includes a single set of sensors to capture the position of an eye of interest, e.g., the eye that is fixating on a target.

In some embodiments, the system is configured to terminate the assessment/measurement test whenever fixation inaccuracy is detected to ensure accuracy of eye fixation during the visual-field assessment/measurement test. That is, the stimulus display remains on the screen if fixation is accurate until the subject finishes providing inputs for the visual-field assessment/measurement.

In other embodiments, the system is configured to generate an audible output, a visual output, or a vibration, to indicate the fixation inaccuracy.

FIG. 23 shows an experimental setup of the system of FIG. 21 configured with the one or more eye tracking sensors or scanners 2102, in accordance with an illustrative embodiment. As shown in FIG. 23, the eye tracking sensors or scanners 2102 comprises a dual camera system that is configured to individually monitor the location of the pupil or cornea of the left eye and the location of the pupil or cornea of the right eye as the eye positions. The system is configured to provide an output when at least one of the eye positions is not located at an expected pre-defined location for a pre-defined duration (e.g., greater than 1-2 degrees or more) during the visual-field assessment/measurement test.

Right-Right Left-Left (RRLL) Phenomenon

In another aspect, the system is configured to contemporaneously capture inputs, from the subject, associated with the subject's observation of a break in a presented pattern at an edge region of the presented display when observed through a blue filter (or other stereoscopic devices). This input is used, in some embodiments, to supplement the visual field assessment/measurement of a subject.

The inventors have observed, in normal subjects and those with less severe visual-field losses, that there is a tendency for a subject to observe a limited region of break in a presented pattern at a farthest edge of the stimulus adjacent to the edge of a presented display. It is also observed that the width of the break may vary as it waxes and wanes like the waves of the ocean. A study was conducted to study this effect. Without wishing to be bound to a particular theory, the observation may be based on a phenomenon associated with the brain processing of visual information (referred to herein as the "Right-eye-right-side left-eye-left-side (RRLL) phenomenon") caused by binocular inhibitory interaction during binocular rivalry (BR) stimulation that is directed by anatomy and neurophysiology of the brain.

More specifically, the inventors have observed that the location of the break at a side of the edge of the display is only observed by the subject's non-tested eye that is viewing the impoverished image through a blue filter (or other stereoscopic devices). Specifically, the subject will observe the effect on the right edge of a presented display when the right eye (RE) is viewing the impoverished image through the blue filter and is observed on the left edge when the left eye (LE) is viewing the impoverished image through the blue filter. Indeed, the system can be configured to capture inputs from the subject in which the capture is associated with an observed break at a left edge of the presented display as observed by a left eye (e.g., when viewing through a blue filter) or an observed break at a right edge of the presented display as observed by a right eye (e.g., when viewing through a blue filter).

By contemporaneously capturing inputs, from the subject, associated with the subject's observation of a break in a presented pattern at an edge region of the presented display when observed through a blue filter, the system can exploit the RRLL phenomenon to augment the interpretation of the visual-field measurement and/or assessment. Specifically, when a RRLL phenomenon is observed, a given assessment can conclude that the visual field is not severely defective. The RRLL phenomenon is distinct from a visual-field loss in that the break in the test pattern in the former waxes and wanes whereas the break in the test pattern in the latter is stable.

Figure 24:
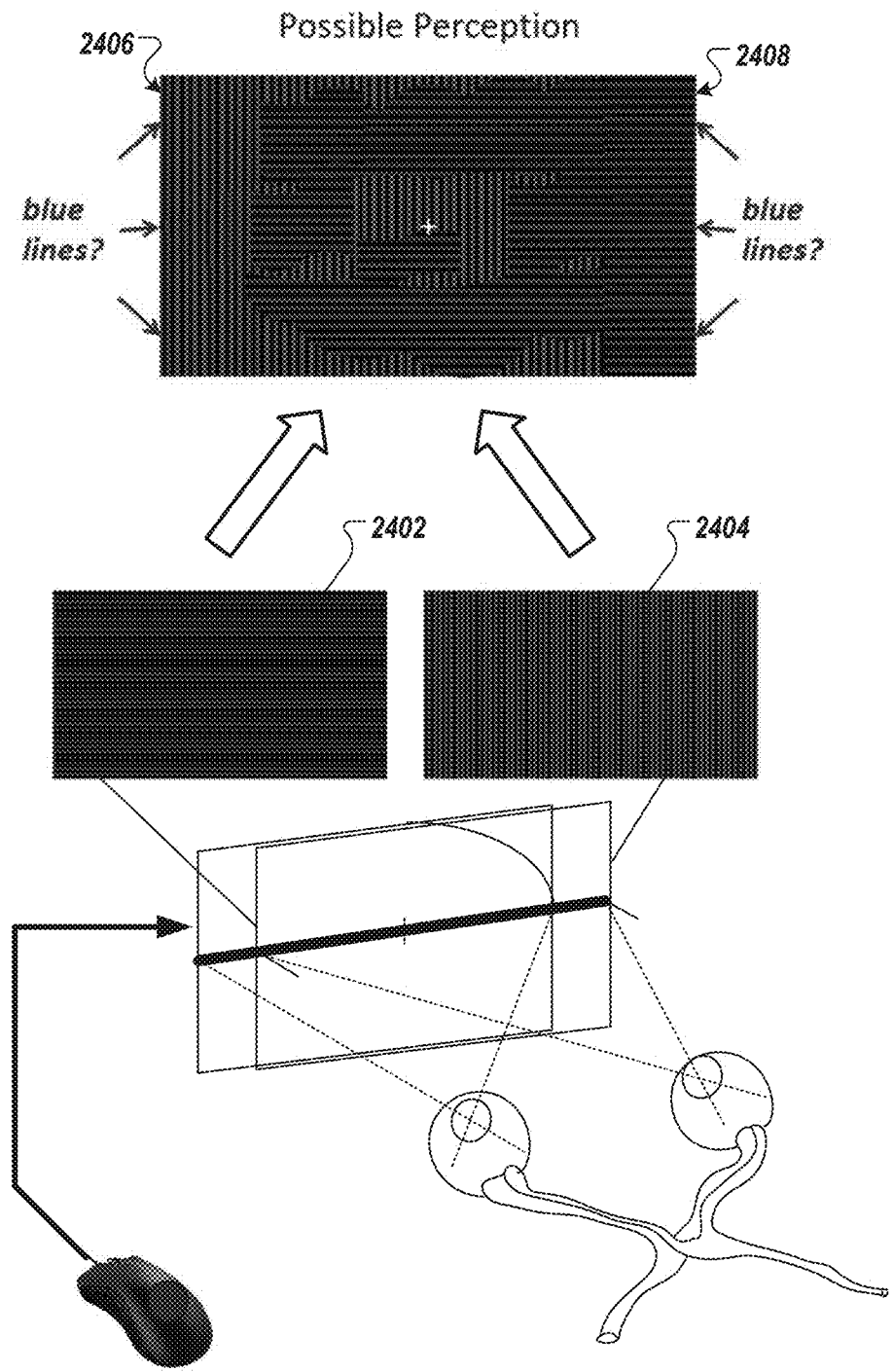
FIG. 24 shows the system of FIG. 3 configured to assess the auxiliary observations to assess for RRLL phenomenon associated with the brain processing of visual information in accordance with an illustrative embodiment.

FIG. 24 shows the system of FIG. 3 configured to assess the auxiliary observations to assess for RRLL phenomenon associated with the brain processing of visual information in accordance with an illustrative embodiment. As shown in FIG. 24, the system 100 is configured to present, to a subject, dissimilar visual scenes in which a first scene 2402 includes a first image having a first pattern and the second scene 2404 includes a second image having a second pattern (e.g., that is orthogonal to the first image). In addition to, or as a substitute for, the system receiving inputs from the subject associated with an observed break in the dissimilar visual scene 102, the system is configured to receive inputs relating to the presence of blue lines being observed at edges (shown as 2406 or 2408) of the presented display. In some embodiments, the system is configured to receive a first input (e.g., a left arrow keyboard button) to connote the presence of a blue line being observed at the edge by the left eye and a second input (e.g., a right arrow keyboard button) to connote the presence of a blue line being observed at the edge by the right eye. In some embodiments, the system is further configured to receive a third input (e.g., a down-arrow keyboard button) to connote if the subject is uncertain whether a blue line is observed at either the left or right edge of the display. In other embodiments, the system is configured to receive a first input (e.g., a first button) to indicate that the subject has observed a blue line either at the left or right edge of the display and a second input (e.g., a second button) to indicate that the subject has not observed, or is unsure of, a blue line either at the left or right edge of the display.

To avoid, or minimize, binocular rivalry alternation, the system, in some embodiments, is configured to present the stimulation for at least about 400 milliseconds or for other duration sufficient to induce binocular suppression while discouraging binocular rivalry alternation.

FIG. 24 further shows the system of FIG. 3 (as well as FIGS. 4, 21 and 22) being configured to present alternative set of dissimilar visual scenes in which each of first image 102 (shown as 2402) and the second image 106 (shown as 2404) has contour patterns but the contour pattern of the first image 2402 is orthogonal to the contour pattern of the second image 2404.

Figure 25:
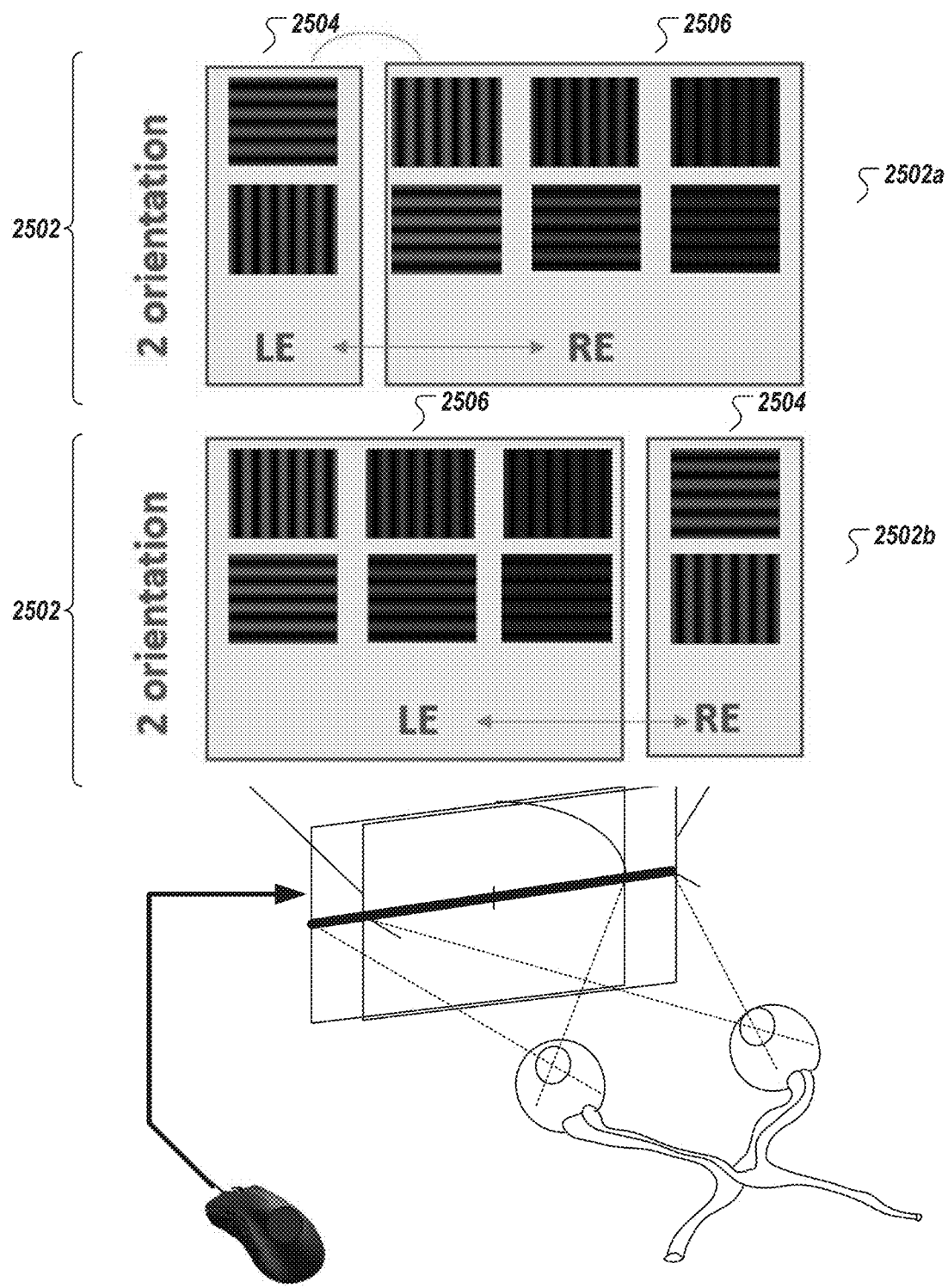
FIG. 25 shows the system of FIG. 3 (as well as FIGS. 4, 21, and 22) being configured to present dissimilar visual scenes in which first image and the second image are varied by orientation of contours and luminance/contrast levels, in accordance with an illustrative embodiment.

FIG. 25 shows the system of FIG. 3 (as well as FIGS. 4, 21, and 22) being configured to present dissimilar visual scenes in which first image and the second image are varied by orientation of contours and luminance/contrast levels, in accordance with an illustrative embodiment.

As shown in FIG. 25, 12 combinations of dissimilar visual scenes can be generated, e.g., by having the first image 102 (shown as "LE" 2504) having a constant luminance/contrast and a first contour pattern in a first orientation and the second image 106 (shown as "RE" 2506) having one of three potential luminance/contrast levels and a second contour pattern in a second orientation that is different (e.g., orthogonal) to the first contour pattern. The first image 2504 can be presented to the left eye and the second image 2506 presented to the right eye in a first instance (2502a) and then switched in which the first image 2504 can be presented to the right eye and the second image 2506 presented to the left eye in a second instance (2502b). In some embodiments, the system generates the first image 102 and second image 106 with a vertical and horizontal sinusoidal gratings, e.g., with 1 cycle per deg (cpd). In other embodiments, the system generates the first image 102 and second image 106 with a first direction sinusoidal grating (e.g., 45 degrees) and a second direction sinusoidal gratings (e.g., −45 degrees).

In some embodiments, the system generates the first image 102 and second image 106 with two colors (e.g., red and blue) in which each image has sufficient luminance for viewing (e.g., between about 2.14 and 10.5 cd/m$^2$).

Having thus described several embodiments of the claimed invention, it will be rather apparent to those skilled in the art that the foregoing detailed disclosure is intended to be presented by way of example only, and is not limiting. Many advantages for non-invasive method and system for locating an abnormality in the visual field have been discussed herein. Various alterations, improvements, and modifications will occur and are intended to those skilled in the art, though not expressly stated herein. Any alterations, improvements, and modifications are intended to be suggested hereby, and are within the spirit and the scope of the claimed invention. Additionally, the recited order of the processing elements or sequences, or the use of numbers, letters, or other designations therefore, is not intended to limit the claimed processes to any order except as may be specified in the claims. Accordingly, the claimed invention is limited only by the following claims and equivalents thereto.

What is claimed is:

1. A method for measuring or assessing human visual field comprising:
    presenting, via a user interface, a human visual field test that stimulates both eyes of a person with dissimilar visual scenes via a controlled vision device, wherein a first set of images includes a first static image that is presented to a first eye of the person, wherein the first static image comprises a first portion of a dichoptic target comprising a first pattern having one or more contour elements that span an entirety of the first image, and wherein a second set of images includes a second portion of the dichoptic target comprising a second static image that is contemporaneously presented to a second eye of the person, wherein the second static image comprises a second pattern having either one or more different distinguishing contour elements to the first static image or no contour elements that spans an entirety of the second static image;
    contemporaneous with the person viewing both the first and second static images and fixating on the dichoptic target, or immediately thereafter, capturing via an electronic display or paper showing at least a portion of the presented pattern of a fused static first and second image one or more inputs from the person, wherein the one or more inputs include an identification of a presence and/or location and/or size of a gap or break in the presented pattern of the fused static first and second image as observed by the person, and wherein the one or more inputs are associated with edges of the gap or break in the observation of the presented pattern by the person, and wherein the gap or break is inputted by the person onto the electronic display or paper from the person's memory subsequent to presentation of the pattern; and
    determining, by a processor configured to receive the one or more inputs captured via the display or paper, a visual field assessment comprising a presence or non-presence of visual field loss or defect for the first eye based on the presence and/or location and/or size of the gap or break in observation of the presented pattern by the person as captured from the one or more inputs, wherein the presented pattern does not include the gap or break, and wherein the visual field assessment is used to provide an indication of at least one of (i) a visual field loss in one or both eyes of the person and (ii) a visual field defect in the first eye of the person,
    wherein the controlled vision device is selected from a group consisting of: a haploscopic device, a stereoscopic device, eyeglasses configured with one or more anaglyphic colored filters for use with an electronic display or a printed material that are configured to appropriately display sets of images as anaglyphic colored images, eyeglasses configured with one or more polarized filters for use with the electronic display or the printed material that are configured to appropriately display sets of images as polarized images, a phase-haploscopic goggle, a 3D virtual-reality head gear, and an augmented reality glass wear.

2. The method of claim 1, wherein the electronic display or paper comprises paper.

3. The method of claim 2, wherein the paper is scanned prior to determining the visual field assessment.

4. The method of claim 2, wherein the one or more inputs comprises a graphical or keyed input received on the paper, and wherein the graphical or keyed input is associated with landmarks presented with or on the first set of images.

5. The method of claim 1, wherein the first set of images are presented with temporal modulation or with contrast modulation.

6. The method of claim 1, wherein the first set of images are presented as a single static image.

7. The method of claim 1, wherein the dichoptic target is placed in a location selected from the group consisting of a center field of the first set of images, a first corner field associated with a first quadrant of the first set of images, a second corner field associated with a second quadrant of the first set of images, a third corner field associated with a third quadrant of the first set of images, and a fourth corner field associated with a fourth quadrant of the first set of images.

8. The method of claim 1, wherein stimulation of the dissimilar visual scenes is with the controlled vision device that provides separate visualization of the first set of images by the first eye and the second set of images by the second eye.

9. The method of claim 1, wherein the first pattern having the one or more contour elements is continuously presented over an entirety of the first set of images.

10. The method of claim 1, wherein the assessment of the person's visual field is selected from the group consisting of:
    a sensitivity assessment of each of the first eye and the second eye;
    a pattern deviation index assessment;
    an assessment of difference in sensitivity between the first eye and the second eye; and
    a ratio assessment of the sensitivity between first eye and a summation of both eyes' sensitivity.

11. The method of claim 1, wherein at least one of the first set of images is configured to span at least 56 degrees of a horizontal field of view of a normal person and to span at least a 33 degrees of vertical field of view of a normal person.

12. The method of claim 1, wherein the first pattern having the one or more contour elements comprises a plurality of concentric circles.

13. The method of claim 1, wherein the first pattern having the one or more contour elements comprises a plurality of radial lines and one or more circles, wherein the plurality of radial lines and the one or more circles define identifiable landmarks to identify presence and/or location and/or size of a gap or break in the observation of the presented pattern.

14. The method of claim 1, further comprising:
generating, by a processor, a simulated visual-field loss stimulation within the first pattern having the one or more contour elements of the first set of images, wherein the simulated visual-field loss stimulation are presented to at least one eye of the person;
capturing, by the processor and via the electronic display or paper, one or more second inputs from the person associated with the presented visual-field loss stimulation as observed by the person; and
determining, by the processor, one or more correlation values between the one or more second inputs and the presented visual-field loss stimulation, wherein the one or more correlation values are indicators of accuracy for the one or more second inputs, and wherein at least one of the one or more correlation values are used to stop or reject the measurement or assessment.

15. The method of claim 1, further comprising:
determining, by a processor, one or more eye positions of at least one eye of the person when the person is fixating on the dichoptic target, wherein deviation of the determined eye position from an expected position of the eye is used to assess eye fixation accuracy or to terminate presentation of a portion of the dissimilar visual scenes.

16. The method of claim 1, further comprising:
contemporaneous with the person fixating on the dichoptic target, directly or indirectly capturing one or more third inputs from the person, wherein the capture is associated with an observed break at a left edge by a left eye or an observed break at a right edge by a right eye.

17. A non-transitory computer readable medium having instructions stored thereon, wherein execution of the instructions by a processor, cause the processor to:
present, via a user interface of an imaging device, a human visual field test that stimulates both eyes of a person with dissimilar visual scenes, wherein a first set of images includes a first static image that is presented, through the user interface of the imaging device, to a first eye of the person, wherein the first static image comprises a first portion of a dichoptic target comprising a first pattern having one or more contour elements that span an entirety of the first image, and wherein a second set of images includes a second portion of the dichoptic target comprising a second static image that is contemporaneously presented, through the user interface of the imaging device, to a second eye of the person, wherein the second static image comprises a second pattern having either one or more different distinguishing contour elements to the first static image or no contour elements that spans an entirety of the second static image;
contemporaneous with the person viewing both the first and second static images and fixating on the dichoptic target, or immediately thereafter, capture via an electronic display or paper showing at least a portion of the presented pattern of a fused static first and second image one or more inputs from the person, wherein the one or more inputs include an identification of a presence and/or location and/or size of a gap or break in the presented pattern of the fused static first and second image as observed by the person, and wherein the one or more inputs are associated with edges of the gap or break in the observation of the presented pattern by the person, and wherein the gap or break is inputted by the person onto the electronic display or paper from the person's memory subsequent to presentation of the pattern; and
determine a visual field assessment based on analysis of the one or more inputs captured via the display or paper, the visual field assessment comprising a presence or non-presence of visual field loss or defect for the first eye based on the presence and/or location and/or size of the gap or break in observation of the presented pattern by the person, as captured from the one or more inputs, wherein the presented pattern does not include the gap or break, and wherein the visual field assessment is used to provide an indication of at least one of (i) a visual field loss in one or both eyes of the person and (ii) a visual field defect in the first eye of the person,
wherein the imaging device is selected from a group consisting of: a haploscopic device, a stereoscopic device, eyeglasses configured with one or more anaglyphic colored filters for use with an electronic display or a printed material that are configured to appropriately display sets of images as anaglyphic colored images, eyeglasses configured with one or more polarized filters for use with the electronic display or the printed material that are configured to appropriately display sets of images as polarized images, a phase-haploscopic goggle, a 3D virtual-reality head gear, and an augmented reality glass wear.

18. A system comprising:
an imaging device;
a processor; and
a memory having instructions stored thereon, wherein execution of the instructions by the processor causes the processor to:
present, via a user interface of the imaging device, a human visual field test that stimulates both eyes of a person with dissimilar visual scenes, wherein a first set of images includes a first static image that is presented, through the user interface of the imaging device, to a first eye of the person, wherein the first static image comprises a first portion of a dichoptic target comprising a first pattern having one or more contour elements that span an entirety of the first image, and wherein a second set of images includes a second portion of the dichoptic target comprising a second static image that is contemporaneously presented, through the user interface of the imaging device, to a second eye of the person, wherein the second static image comprises a second pattern having either one or more different distinguishing contour elements to the first static image or no contour elements that spans an entirety of the second static image; and
contemporaneous with the person viewing both the first and second static images and fixating on the dichoptic target, or immediately thereafter, capture via an electronic display or paper showing at least a portion of the presented pattern of a fused static first and second image one or more inputs from the person, wherein the one or more inputs include an identification of a presence and/or location and/or size of a gap or break in the presented pattern of the fused static first and second image as observed by the person, and wherein the one or more inputs are associated with edges of the gap or break in the observation of the presented pattern by the person, and wherein the gap or break is inputted by the person onto the electronic display or paper from the person's memory subsequent to presentation of the pattern; and determine a visual field assessment based on analysis of the one or more inputs captured via the display or paper, the visual field assessment comprising a presence or non-presence of visual field loss or defect for the first eye based on the presence and/or location and/or size of the gap or break in observation of the presented pattern by the person, as captured from the one or more inputs, wherein the presented pattern does not include the gap or break, and wherein the visual field assessment is used to provide an indication of at least one of (i) a visual field loss in one or both eyes of the person and (ii) a visual field defect in the first eye of the person wherein the imaging device is selected from a group consisting of: a haploscopic device, a stereoscopic device, eyeglasses configured with one or more anaglyphic colored filters for use with an electronic display or a printed material that are configured to appropriately display sets of images as anaglyphic colored images, eyeglasses configured with one or more polarized filters for use with the electronic display or the printed material that are configured to appropriately display sets of images as polarized images, a phase-haploscopic goggle, a 3D virtual-reality head gear, and an augmented reality glass wear.

19. The system of claim 18, further comprising:

an eye tracking module configured to measure one or more eye positions of the person while the person is contemporaneously fixating on the dichoptic target.

* * * * *